United States Patent
Wu et al.

(10) Patent No.: US 11,497,747 B2
(45) Date of Patent: Nov. 15, 2022

(54) COMPOSITIONS AND METHODS FOR TREATING LUNG INJURIES ASSOCIATED WITH SARS-COV-2 INFECTIONS

(71) Applicant: Qx Therapeutics Inc., Branford, CT (US)

(72) Inventors: Dianqing Wu, New Haven, CT (US); Ho Yin Lo, Bethel, CT (US)

(73) Assignees: Qx Therapeutics Inc., Branford, CT (US); Yale University, New Haven, CT (US)

( * ) Notice: Subject to any disclaimer, the term of this patent is extended or adjusted under 35 U.S.C. 154(b) by 0 days.

(21) Appl. No.: 17/697,448

(22) Filed: Mar. 17, 2022

(65) Prior Publication Data
US 2022/0202816 A1    Jun. 30, 2022

Related U.S. Application Data

(63) Continuation of application No. 17/325,968, filed on May 20, 2021, now Pat. No. 11,304,947.

(60) Provisional application No. 63/029,375, filed on May 22, 2020.

(51) Int. Cl.
| | | |
|---|---|---|
| *A61K 31/506* | (2006.01) | |
| *A61K 31/496* | (2006.01) | |
| *A61P 11/00* | (2006.01) | |
| *A61P 31/14* | (2006.01) | |
| *A61K 31/675* | (2006.01) | |

(52) U.S. Cl.
CPC .......... *A61K 31/506* (2013.01); *A61K 31/496* (2013.01); *A61K 31/675* (2013.01); *A61P 11/00* (2018.01); *A61P 31/14* (2018.01)

(58) Field of Classification Search
CPC .................................................. A61K 31/506
See application file for complete search history.

(56) References Cited

U.S. PATENT DOCUMENTS

| | | |
|---|---|---|
| 6,762,180 B1 | 7/2004 | Roth et al. |
| 7,105,530 B2 | 9/2006 | Boloor et al. |
| 7,119,093 B2 | 10/2006 | Roth et al. |
| 7,262,203 B2 | 8/2007 | Boloor et al. |
| 7,858,626 B2 | 12/2010 | Boloor et al. |
| 8,114,885 B2 | 2/2012 | Boloor et al. |
| 2013/0289014 A1* | 10/2013 | Solca .................. A61K 31/496 514/235.8 |
| 2015/0224132 A1 | 8/2015 | Appleman et al. |
| 2020/0384034 A1* | 12/2020 | Glassberg Csete .. C12Q 1/6883 |
| 2020/0384038 A1 | 12/2020 | Grant et al. |
| 2021/0121459 A1 | 4/2021 | Wu et al. |

FOREIGN PATENT DOCUMENTS

| | | |
|---|---|---|
| WO | 2015120350 A2 | 8/2015 |
| WO | 2018195084 A1 | 10/2018 |

OTHER PUBLICATIONS

Wolff et a. (1994).*
Vlppagunta et al. (2000).*
Banker et al. (1997).*
Flaherty, K.R. et al. "Nintedanib in Progressive Fibrosing Interstitial Lung Diseases", 2019, The New England Journal of Medicine, 381:18, pp. 1718-1727.
International Search Report, PCT/US2021/033418, dated Sep. 15, 2021.
Brower, R.G., et al., "Ventilation with lower tidal volumes as compared with traditional tidal volumes for acute lung injury and the acute respiratory distress syndrome." New England Journal of Medicine, 2000. 342(18): p. 1301-1308.
De Albuquerque, N., et al.,"Murine hepatitis virus strain 1 produces a clinically relevant model of severe acute respiratory syndrome in NJ mice." J Virol, 2006. 80(21): p. 10382-94.
Ding, Y., et al., "The clinical pathology of severe acute respiratory syndrome (SARS): a report from China." J Pathol, 2003. 200(3): p. 282-9.
Johnson, E.R. and M.A. Matthay, "Acute Lung Injury: Epidemiology, Pathogenesis, and Treatment." Journal of Aerosol Medicine and Pulmonary Drug Delivery, 2010. 23(4): p. 243-252.
Maca, J., et al., "Past and Present ARDS Mortality Rates: A Systematic Review." Respir Care, 2017. 62(1): p. 113-122.
Matthay, M.A. and R.L. Zemans, "The acute respiratory distress syndrome: pathogenesis and treatment." Annu Rev Pathol, 2011.6: p. 147-63.
Minocha, M., V. Khurana, and A.K. Mitra, "Determination of pazopanib (GW-786034) in mouse plasma and brain tissue by liquid chromatography-tandem mass spectrometry (LC/MS-MS)." J Chromatogr B Analyt Technol Biomed Life Sci, 2012. 901: p. 85-92.
Ng, D.L., et al., "Clinicopathologic, Immunohistochemical, and Ultrastructural Findings of a Fatal Case of Middle East Respiratory Syndrome Coronavirus Infection in the United Arab Emirates, Apr. 2014." Am J Pathol, 2016. 186(3): p. 352-8.
Tian, S., et al., "Pulmonary Pathology of Early-Phase 2019 Novel Coronavirus (COVID-19) Pneumonia in Two Patients With Lung Cancer." J Thorac Oncol, 2020.

(Continued)

*Primary Examiner* — Paul V Ward
(74) *Attorney, Agent, or Firm* — Wiggin and Dana LLP; Anthony D. Sabatelli

(57) ABSTRACT

The present invention provides methods and compositions for treating and preventing lung injuries due to or associated with coronavirus infections that cause Severe Acute Respiratory Syndrome, including COVID-19. More specifically the present invention provides methods for treating or preventing the lung injuries associated with SARS-CoV-2 infections, such as acute lung injury (ALI), lung fibrosis, and acute respiratory distress syndrome (ARDS). The methods comprise administering a therapeutically effective amount of a pharmaceutical composition comprising a protein kinase inhibitor compound having MAP3K2/MAP3K3 inhibition activity, such as pazopanib or nintedanib, or a pharmaceutically acceptable salt, solvate, or prodrug thereof, to a patient in need thereof. The present invention also provides devices for administering the compositions.

31 Claims, 7 Drawing Sheets

(56) References Cited

OTHER PUBLICATIONS

Weinert, C.R., C.R. Gross, and W.A. Marinelli, "Impact of randomized trial results on acute lung injury ventilator therapy in teaching hospitals." American Journal of Respiratory and Critical Care Medicine, 2003. 167(10): p. 1304-1309.
Xu, Z., et al., "Pathological findings of COVID-19 associated with acute respiratory distress syndrome." The Lancet Respiratory Medicine, 2020.
Yuan, Q. et al. "Pazopanib ameliorates acute lung injuries via inhibition of MAP2K2 and MPA3K3", Science Translational Medicine, 13, eabc2499, published Apr. 28, 2021.
FDA Route of Administration, Retrieved from the Internet, URL: www.fda.gov/drugs/data-standards-manual-monographs/route-administration, Retrieved on Jul. 8, 2021.
Highlights of Prescribing Information, VOTRIENT, May 2017.
Votrient Safety Information, Retrieved from the Internet, URL: www.hcp.novartis.comiproductsivotrienti?site=VRT-12 18078GK1002528source=01030&gclid=EAlalQobChMI4-obj5KvD6QIVkIbACh00EAS4EAAYASAAEgKnRvD_BwE&gclsrc= aw.ds, Retrieved on Jul. 8, 2021.

\* cited by examiner

COMPOSITIONS AND METHODS FOR TREATING LUNG INJURIES ASSOCIATED WITH SARS-COV-2 INFECTIONS

CROSS-REFERENCE TO RELATED APPLICATIONS

This application is a continuation of U.S. patent application Ser. No. 17/325,968 filed May 20, 2021, which claims the benefit of the filing date of U.S. Provisional Application No. 63/029,375, filed May 22, 2020, all of which are herein incorporated by reference in their entirety.

FIELD OF THE INVENTION

The present invention provides methods and compositions for treating and preventing lung injuries due to or associated with coronavirus infections that cause Severe Acute Respiratory Syndrome, including COVID-19. More specifically the present invention provides methods for treating or preventing the lung injuries associated with SARS-CoV-2 infections, such as acute lung injury (ALI), lung fibrosis, and acute respiratory distress syndrome (ARDS). The methods comprise administering a therapeutically effective amount of a pharmaceutical composition comprising a protein kinase inhibitor compound having MAP3K2/MAP3K3 inhibition activity, such as pazopanib or nintedanib, or a pharmaceutically acceptable salt, solvate, or prodrug thereof, to a patient in need thereof. The present invention also provides devices for administering the compositions.

BACKGROUND OF THE INVENTION

Coronavirus disease 2019, also known as COVID-19, is an infectious disease caused by the Severe Acute Respiratory Syndrome Corona Virus 2 (SARS-CoV-2). The disease was first identified in 2019 in Wuhan, Hubei province, China. As of early May 2020, more than 3.48 million cases have been reported across 187 countries and territories, resulting in more than 246,000 deaths. See, COVID-19 Dashboard by the Center for Systems Science and Engineering (CSSE) at Johns Hopkins University (JHU)". ArcGIS. Johns Hopkins University. May 3, 2020.

Common symptoms of coronavirus infections include fever, cough, fatigue, shortness of breath, and loss of smell and taste. Even though the majority of cases result in mild symptoms, some progress to viral pneumonia, multi-organ failure, cytokine storm, and permanent tissue and organ damage, such as lung damage, and death. The disease can be particularly serious with poor outcomes for those most at risk. Some of the more serious risk factors include asthma, chronic lung disease, diabetes, serious heart conditions, chronic kidney disease being treated with dialysis, severe obesity, people aged 65 years and older, people in nursing homes or long-term care facilities, and those who are immunocompromised (such as patients undergoing cancer chemotherapy or transplant recipients). The time from exposure to onset of symptoms is typically around five days but can range from two to fourteen days.

The disease is highly contagious. The virus is primarily spread between people during close contact, often via small droplets produced by coughing, sneezing, or even during speaking. On surfaces, the virus can remain active for several hours or days and people can become infected by touching a contaminated surface and then touching their face, where the virus can enter the body through the nose, mouth, eyes or ears. A carrier of the disease is generally most contagious during the first three days of symptoms, but may spread the disease before symptoms appear or asymptomatically. The standard method of diagnosis is by real-time reverse transcription polymerase chain reaction (rRT-PCR) from a nasopharyngeal swab.

As of May 1, 2020, no drugs or other therapeutics have been approved by the U.S. Food and Drug Administration (FDA) to prevent or treat coronavirus infections. Current clinical management includes infection prevention and control measures and supportive care, including supplemental oxygen and mechanical ventilatory support when indicated. Treatment is managed to control symptoms and to provide palliative care. For severe cases requiring hospitalization, and in particular those requiring admission to an intensive care unit (ICU), mechanical ventilation may be required if blood oxygen levels become too low. However, despite the benefits of mechanical ventilation, there is the risk of ventilator-associated lung injury and pneumothorax, i.e. lung collapse.

Two medications, hydroxychloroquine and chloroquine, which have been used to treat malaria and autoimmune conditions such as rheumatoid arthritis and lupus have been used on an experimental basis. However, as of May 1, 2020, there has not been definitive medical data demonstrating the effectiveness of hydroxychloroquine and chloroquine. Furthermore, the antiviral remdesivir is being explored as a treatment, based on in vitro and in vivo activity in animal models against structurally similar viral pathogens. However, currently, the most currently effective measures for addressing coronavirus infections are focused on disease prevention and spread and include hand washing, wearing of face coverings, social distancing, and quarantining.

A consequence of coronavirus infections is the acute lung injury (ALI) and acute respiratory distress syndrome (ARDS) which can result from a severe case of infection. ALI and ARDS are the manifestations of an inflammatory response of the lung to direct or indirect insults, and are characterized by severe hypoxemia and a substantial reduction in pulmonary compliance due to diffuse alveolar damage, neutrophilic inflammation, and protein-rich edema in the lungs. ALI and ARDS have a very high mortality rate of about 40%. Care of these conditions is largely dependent on supportive measures and there is currently a lack of effective pharmacological interventions. Prior pharmacological therapies that have been tested in patients with ALI/ARDS failed to reduce mortality. There is thus a clear unmet medical need for therapeutic intervention of the ALI and ARDS that is often associated with a severe coronavirus infection.

One of the hallmarks of ALI is the abundant presence of neutrophils in the lungs. Neutrophils are the most abundant leukocytes in human circulation, playing important roles in innate immunity against microbial infections and also contributing to inflammation-related tissue damage. During the inflammation, neutrophils are recruited to the sites of injury and infection from circulation through a multi-step process, which includes rolling and firm adhesion on endothelial cells, intravascular crawling, diapedesis, and extravascular chemotaxis. Once at the sites, neutrophils perform a number of tasks including phagocytosis, release of preformed granule enzymes, and production of reactive oxygen species (ROS). Evidence has clearly linked neutrophils to the pathogenesis of ALI/ARDS. Although crossing of the alveolar epithelium by neutrophils does not directly cause an increase in lung epithelial permeability, neutrophils play important roles in pulmonary edema with the underlying mechanisms that remain incompletely understood.

While neutrophil extracellular traps and granule enzymes such as neutrophil elastase contribute to the pathology of ALI, including lung edema, any role of ROS in ALI/ARDS is still debatable. Neutrophils produce ROS primarily through the phagocyte NADPH oxidase, which is a member of the NOX family. This family consists of four cytosolic components ($p47^{phox}$, $p67^{phox}$, $p40^{phox}$, and Rac) and two membrane subunits ($gp91^{phox}$/NOX2 and $p22^{phox}$). When the cells are activated by stimuli such as chemo-attractants, the cytosolic components are recruited to the membrane components to form the active holoenzyme to produce ROS. One of the key activation events is the phosphorylation of the cytosolic $p47^{phox}$ subunit by protein kinases including PKC. The phosphorylation disrupts auto-inhibitory intramolecular interaction involving the internal SH3 domains, leading to its interaction with $p22^{phox}$ required for the activation of the NADPH oxidase. MAP3K2 and MAP3K3 are two highly conserved members of the MEK kinase (MEKK) subgroup of the MAP3K superfamily, and contain a kinase domain in the C terminus and a PB1 domain near the N terminus. The kinase domains of MAP3K2 and MAP3K3 share 94% sequence identity, and these two kinases are expected to share substrates. Transient expression of the kinases in vitro leads to their auto-activation and activation of ERK1 and ERK2, p38, JNK, and ERK5. In mice, these kinases are involved in cardiovascular development, lymphocyte differentiation and NF-kappaB regulation. However, their roles in primary myeloid cell biology or ALI have not been investigated. It had previously been found that the MAP3K2/MAP3K3 inhibitor, pazopanib, provides a method of treating or preventing acute lung injury and treating or preventing lung fibrosis. See WO 2018/195084, to Wu et al., published Oct. 25, 2018.

Pazopanib is a small molecule inhibitor that was originally identified as inhibiting multiple protein tyrosine kinases with potential antineoplastic activity. Pazopanib selectively inhibits vascular endothelial growth factor receptors (VEGFR)-1, -2 and -3, c-kit and platelet derived growth factor receptor (PDGF-R), which may result in inhibition of angiogenesis in tumors in which these receptors are upregulated. It is used in the therapy of advanced renal cell carcinoma and soft tissue sarcomas. Pazopanib is known by the trade name Votrient® and is marketed by Novartis as an oral tablet formulation. Pazopanib is also a $p47^{phox}$ substrate-specific inhibitor of MAP3K2/MAP3K3. Pazopanib inhibits MAP3K2/MAP3K3-mediated phosphorylation of $p47^{phox}$ at low nM levels while inhibiting other substrates of MAP3K2/MAP3K3 such as MEK5 at µM levels. See Ibid., WO 2018/195084. In addition to pazopanib, nintedanib, which is sold under Trade names OFEV and Vargatef and which is marketed by Boehinger Ingelheim also inhibits MAP3K2/MAP3K3-mediated phosphorylation of $p47^{phox}$ and has been shown to reduce ALI in mouse models. While pazopanib and nintedanib are inhibitors of tyrosine kinases, many other similar tyrosine kinase inhibitors, including imatinib, do not inhibit MAP3K2/MAP3K3-mediated phosphorylation of $p47^{phox}$ nor reduce ALI in mouse models.

It is therefore seen there is an urgent and unmet need to treat or prevent lung injuries which can be due to or associated with infections such as coronavirus. The present invention provides methods and compositions for treating or preventing such lung injuries comprising administering a therapeutically effective amount of a pharmaceutical composition to a subject in need thereof of a comprising a compound capable of inhibiting MAP3K2 and/or MAP3K3.

SUMMARY OF THE INVENTION

The present invention provides methods and compositions for treating or preventing lung injuries due to or associated with viral infections. The methods comprise administering a therapeutically effective amount of a pharmaceutical composition to a subject in need thereof comprising a MAP3K2/MAP3K3 inhibitor, such as pazopanib or nintedanib, or a pharmaceutically acceptable salt, solvate, or prodrug thereof to a patient in need thereof. More specifically, the present invention provides methods and compositions for treating and preventing lung injuries associated with coronavirus infections that cause Severe Acute Respiratory Syndrome including COVID-19.

Examples of useful compositions comprise those which can be delivered using an administration route such as oral, oropharyngeal, parenteral, nasal, respiratory (inhalation), intraperitoneal, intrapleural, intravenous, lanyngeal, topical, transdermal, transmucosal intratracheal, intrapulmonary, and intrabronchial. The present invention also provides devices for administering these compositions to the patient.

In some embodiments the present invention provides:

A method for treating, preventing, or reducing the severity of a lung injury associated with and/or due to a viral infection comprising administering a therapeutically effective amount of a pharmaceutical composition comprising a compound capable of inhibiting MAP3K2/MAP3K3, or a pharmaceutically acceptable salt, ester, solvate, or prodrug thereof to a patient in need thereof.

In further embodiments, the present invention provides:

A method wherein said compound capable of inhibiting MAP3K2/MAP3K3 is selected from the group consisting of pazopanib or nintedanib, and combinations thereof, and pharmaceutically acceptable salts, solvates, or prodrugs thereof.

A method wherein said compound capable of inhibiting MAP3K2/MAP3K3 is pazopanib, or a pharmaceutically acceptable salt, solvate, or prodrug thereof.

A method wherein the pharmaceutically acceptable salt is selected from a salt of a mineral acid selected from the group consisting of hydrochloride, hydrobromide, hydroiodide, hydrogen sulfate, or a salt selected from mesylate, esylate, besylate, tosylate, and combinations thereof.

A method wherein the compound capable of inhibiting MAP3K2/MAP3K3 is pazopanib hydrochloride.

A method wherein the compound capable of inhibiting MAP3K2/MAP3K3 is nintedanib, or a pharmaceutically acceptable salt, solvate, or prodrug thereof.

A method wherein the pharmaceutically acceptable salt of nintedanib is selected from a salt of a mineral acid selected from the group consisting of hydrochloride, hydrobromide, hydroiodide, hydrogen sulfate, or a salt selected from mesylate, esylate, besylate, tosylate, and combinations thereof.

A method wherein the compound capable of inhibiting MAP3K2/MAP3K3 is nintedanib esylate.

A method wherein the compound capable of inhibiting MAP3K2/MAP3K3 is administered using an administration route selected from the group consisting of oral, intravenous, parenteral, nasal, inhalation (i.e. respiratory), intratracheal, intrapulmonary, and intrabronchial.

A method wherein the compound capable of inhibiting MAP3K2/MAP3K3 is administered using an administration route selected from the group consisting of nasal, inhalation (i.e. respiratory), intratracheal, intrapulmonary, and intrabronchial.

A method wherein the administration is performed using a spray device or nebulizer.

A method wherein the patient is a mammal.

A method wherein the patient is a human.

A method wherein the patient is on a ventilator (also known as a respirator or breathing machine).

A method wherein the patient is in an intensive care unit (ICU) or an emergency room (ER).

A method wherein the lung injury is selected from the group consisting of acute lung injury (ALI), lung fibrosis, and acute respiratory distress syndrome (ARDS).

A method wherein the lung injury is acute lung injury (ALI).

A method wherein the lung injury is lung fibrosis.

A method wherein the lung injury is acute respiratory distress syndrome (ARDS).

A method wherein the lung involves pulmonary edema.

A method wherein the pulmonary edema is reduced after treatment.

A method wherein the lung injury involves increased pulmonary permeability.

A method wherein the pulmonary permeability is reduced after treatment.

A method wherein the lung injury involves reduced pulmonary barrier function.

A method wherein the reduced pulmonary barrier function is improved after treatment.

A method wherein the lung injury involves reduced pulmonary barrier cell survival.

A method wherein the reduced pulmonary barrier cell survival is improved after treatment.

A method wherein the time the patient is on a ventilator is reduced after treatment.

A method wherein blood oxygen levels of the patient are returned to within a normal range after treatment.

A method wherein the patient exhibits an increase in rheumatoid factor (RF) production from neutrophils or an increase in reactive oxygen species (ROS) after treatment.

A method wherein the time to recover for the patient is decreased after treatment.

A method wherein the viral infection is caused by the Severe Acute Respiratory Syndrome Corona Virus 2 (SARS-CoV-2).

A method wherein the composition is administered from the group consisting of about four times per day, about three times per day, about two times per day, about one time per day, about one time every other day, about two times per week, and about one time per week.

A method wherein the composition is administered about one time per day.

A method wherein the composition is administered about two times per day.

A method wherein the composition is administered about three times per day.

A method wherein the composition is administered about four times per day.

A method wherein the composition is administered until the infection is treated.

A method wherein the composition is administered for a period from the group consisting of about 1 day to about 30 days [or about one month], about 1 day to about 14 days, about 1 day to about 10 days, about 1 day to about 1 week (7 days), about 1 day to about 5 days, or about 1 day to about 3 days.

A method wherein the composition is administered for a period from about 1 day to about 14 days.

A method wherein at least one of the following pharmacokinetic parameters achieved in the patient is selected from an AUC of about 1,037 mcg*h/mL or a Cmax of about 58.1 mcg/mL (equivalent to about 132 µM) for the compound capable of inhibiting MAP3K2/MAP3K3.

A method wherein the composition comprises from about 1 to about 1000 mg per unit dosage of the compound capable of inhibiting MAP3K2/MAP3K3 based on the active moiety of the compound.

A method wherein the composition comprises about 100 mg, or about 200 mg, or about 300 mg, or about 400 mg, or about 500 mg or about 600 mg, or about 700 mg, or about 800 mg per unit dosage of the compound capable of inhibiting MAP3K2/MAP3K3 based on the active moiety of the compound.

A method further comprising an additional active agent.

A method wherein the additional agent is remdesivir, or a pharmaceutically acceptable salt, ester, solvate, or prodrug thereof.

A pharmaceutical composition for treating, preventing, or reducing the severity of a lung injury associated with a coronavirus infection, comprising:
(a) a therapeutically effective amount of a compound capable of inhibiting MAP3K2/MAP3K3, or a pharmaceutically acceptable salt, ester, solvate, or prodrug thereof, and
(b) a pharmaceutically acceptable carrier.

A composition wherein the compound capable of inhibiting MAP3K2/MAP3K3 is selected from the group consisting of pazopanib or nintendanib, and combinations thereof, or a pharmaceutically acceptable salt, solvate, or prodrug thereof.

A composition that is an aqueous composition.

A composition that is in the form of a dry powder.

A composition for administration via a route selected from the group consisting of nasal, inhalation (i.e. respiratory), intratracheal, intrapulmonary, and intrabronchial.

A composition further comprising an additional active agent.

A composition wherein the additional agent is remdesivir, or a pharmaceutically acceptable salt, ester, solvate, or prodrug thereof.

A device or kit for administration of a composition of the present invention.

The use of a compound capable of inhibiting MAP3K2/MAP3K3, or a pharmaceutically acceptable salt, ester, solvate, or prodrug thereof, in the manufacture of a medicament for delivery of a therapeutically effective amount of a pharmaceutical composition comprising a compound capable of inhibiting MAP3K2/MAP3K3 for treating, preventing, or reducing the severity of a lung injury associated with a viral infection.

A use wherein the viral infection is caused by the Severe Acute Respiratory Syndrome Corona Virus 2 (SARS-CoV-2).

A use wherein said compound capable of MAP3K2/MAP3K3 inhibition is selected from the group consisting of pazopanib or nintedanib, and combinations thereof, or a pharmaceutically acceptable salt, solvate, ester, or prodrug thereof.

A compound capable of inhibiting MAP3K2/MAP3K3, or a pharmaceutically acceptable salt, ester, solvate, or prodrug thereof, for use in treating, preventing, or reducing the severity of a lung injury associated with a viral infection when administered to a subject in need thereof in a therapeutically effective amount.

A compound wherein the viral infection is caused by the Severe Acute Respiratory Syndrome Corona Virus 2 (SARS-CoV-2).

A compound capable of MAP3K2/MAP3K3 selected from the group consisting of pazopanib or nintedanib, and combinations thereof, or a pharmaceutically acceptable salt, solvate, ester, or prodrug thereof.

DETAILED DESCRIPTION OF THE INVENTION

Definitions

Figure 1:
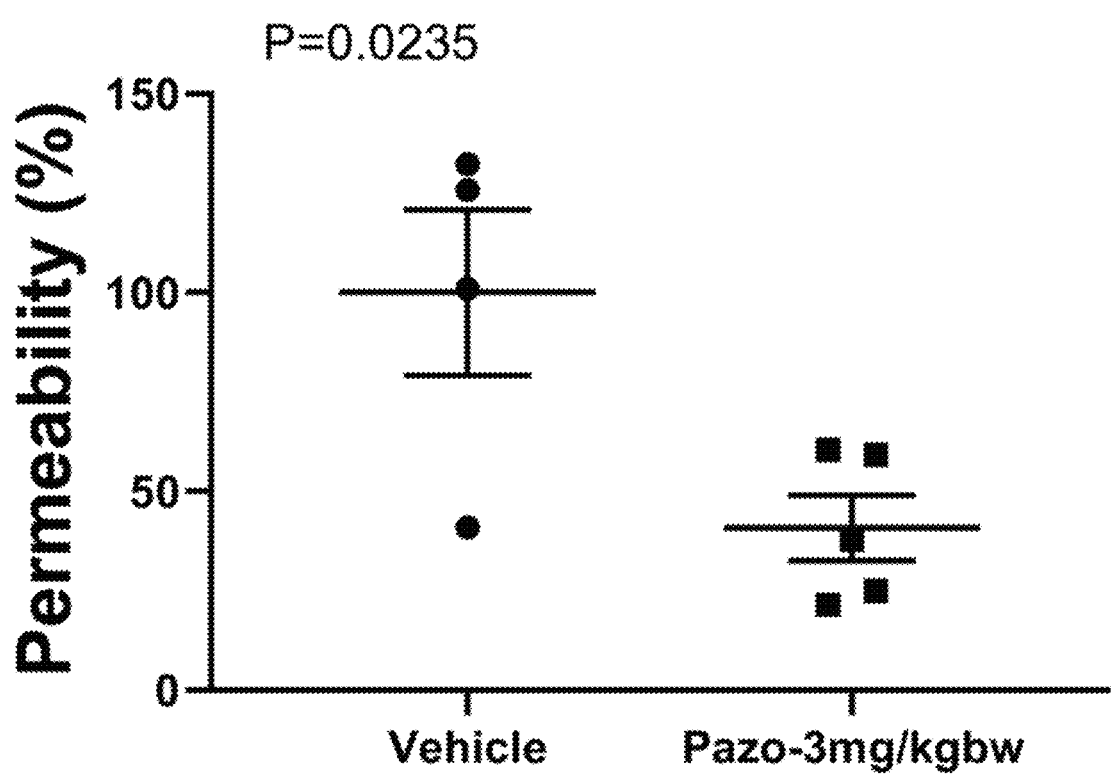
FIG. 1 shows pulmonary permeability in a mouse coronavirus induced acute lung injury model with three doses of a MAP3K2/MAP3K3 inhibitor after virus inoculation.

As used herein, the following terms and abbreviations have the indicated meanings unless expressly stated to the contrary.

The term "compound capable of inhibiting MAP3K2/MAP3K3" means a compound that is an inhibitor of MAP3K2 and/or MAP3K3, i.e. a MAP3K2/MAP3k3 inhibitor. The inhibition of MAP3K2 and/or MAP3K3 can be complete or partial.

The terms "effective", "pharmaceutically effective", and "therapeutically effective" means an amount of a MAP3K2/MAP3K3 inhibitor needed to provide a meaningful or demonstrable benefit, as understood by medical practitioners, to a subject, such as a human patient in need of treatment. Conditions, intended to be treated include, for example, coronavirus infections, including lung injury. For example, a meaningful or demonstrable benefit can be assessed or quantified using various clinical parameters. The demonstration of a benefit can also include those provided by models, including but not limited to in vitro models, in vivo models, and animal models.

The term "inhalation" as used herein also includes the term "respiratory" and means administration within the respiratory tract by inhaling orally or nasally for local or systemic effect.

The term "intranasal" as used herein with respect to the pharmaceutical compositions and actives therein, means a composition that is administered through the nose for delivery across the mucosal membrane inside the nasal cavity. This membrane is a well vascularized thin mucosa. Furthermore, this mucosa is in close proximity to the brain and provides a means to maximize the transport of drugs across the blood-brain barrier. The blood-brain barrier is a highly selective semipermeable border that separates the circulating blood from the brain and extracellular fluid in the central nervous system. Although intranasal administration can be employed for the present invention, it can be preferable in other circumstances to provide delivery directly to the lungs by inhalation/respiratory, or other suitable means.

The U.S. Food & Drug Administration has provided a standard for all routes of administration for drugs, i.e. "Route of Administration". Examples of selected routes that are especially suitable for the present invention are shown below.

| NAME | DEFINITION | SHORT NAME | FDA CODE | NCI* CONCEPT ID |
|---|---|---|---|---|
| INTRABRONCHIAL | Administration within a bronchus. | I-BRONCHI | 067 | C38225 |
| INTRAPERITONEAL | Administration within the peritoneal cavity. | I-PERITON | 004 | C38258 |
| INTRAPLEURAL | Administration within the pleura. | I-PLEURAL | 043 | C38259 |
| INTRAPULMONARY | Administration within the lungs or its bronchi. | I-PULMON | 414 | C38261 |
| INTRAVENOUS | Administration within or into a vein or veins. | IV | 002 | C38276 |
| LARYNGEAL | Administration directly upon the larynx. | LARYN | 364 | C38282 |
| NASAL | Administration to the nose; administered by way of the nose. | NASAL | 014 | C38284 |
| ORAL | Administration to or by way of the mouth. | ORAL | 001 | C38288 |
| OROPHARYNGEAL | Administration directly to the mouth and pharynx. | ORO | 410 | C38289 |
| RESPIRATORY (INHALATION) | Administration within the respiratory tract by inhaling orally or nasally for local or systemic effect. | RESPIR | 136 | C38216 |
| TOPICAL | Administration to a particular spot on the outer surface of the body. | TOPIC | 011 | C38304 |

-continued

| NAME | DEFINITION | SHORT NAME | FDA CODE | NCI* CONCEPT ID |
|---|---|---|---|---|
| TRANSDERMAL | Administration through the dermal layer of the skin to the systemic circulation by diffusion. | T-DERMAL | 358 | C38305 |
| TRANSMUCOSAL | Administration across the mucosa. | T-MUCOS | 122 | C38283 |

*National Cancer Institute
www.fda.gov/drugs/data-standards-manual-monographs/route-administration The term "pharmaceutically acceptable" is used herein with respect to the compositions, in other words the formulations, of the present invention, and also with respect to the pharmaceutically acceptable salts, esters, solvates, and prodrugs thereof. The pharmaceutical compositions of the present invention comprise a therapeutically effective amount of the active agents and a pharmaceutically acceptable carrier. These carriers can contain a wide range of excipients. Pharmaceutically acceptable carriers are those conventionally known carriers having acceptable safety profiles. The compositions are made using common formulation techniques. See, for example, *Remington's Pharmaceutical Sciences*, 17$^{th}$ edition, edited by Alfonso R. Gennaro, Mack Publishing Company, Easton, Pa., 17th edition, 1985. Regarding pharmaceutically acceptable salts, these are described below.

The term "subject" means a human patient or animal in need of treatment or intervention for a coronavirus infection.

The terms "treating" and its derivatives such as "treat" or "treatment," as used herein, may be used with respect to a particular condition, for example, lung injury due to or associated with a viral infection such as a coronavirus infection, including but not limited to, acute lung injury (ALI), lung fibrosis, and/or acute respiratory distress syndrome (ARDS). In reference to a particular condition, "treating" and its derivatives are inclusive of several meanings, including (1) to alleviate one or more symptoms, effects, or side effects associated with the condition, (2) to ameliorate the condition and/or one or more of the biological manifestations or underlying causes of the condition, (3) to interfere with one or more of the biological manifestations or underlying causes of the condition or with one or more points in the biological cascade(s) associated with the condition, (4) to slow the progression of, or arrest the development of, the condition or of one or more of the biological manifestations of the condition, (5) to prevent or reduce the risk of a subject developing the condition, in some cases prophylactically when the subject has one or more risk factors for the condition or has been exposed to or infected with a virus being associated or having potential to cause the condition (6) to cause regression of the condition, or improvement or reversal of, the biological manifestations or underlying causes of the conditions. It can be appreciated that "treating" may encompass one or more of these meanings simultaneously and that a subject's condition may change over time or throughout the course of treatment such that the meaning of "treating" as applied to a given subject may change over time or throughout the course of treatment. "Treatment" could be in combination with other therapies or alone.

Methods

The methods of treatment using a MAP3K2/MAP3K3 inhibitor or a pharmaceutically acceptable salt, solvate ester, or prodrug thereof or the pharmaceutical compositions of the present invention, in various embodiments also include the use of a MAP3K2/MAP3K3 inhibitor or a pharmaceutically acceptable salt, solvate ester, or prodrug thereof in the manufacture of a medicament for the desired treatment, such as for treating or preventing lung injury due to or associated with a COVID-19 infection. Also provided for under methods of treatment are compounds capable of inhibiting MAP3K2/MAP3K3, or a pharmaceutically acceptable salts, esters, solvates, or prodrugs thereof, for use in treating, preventing, or reducing the severity of a lung injury due to or associated with a viral infection when administered to a subject in need thereof in a therapeutically effective amount.

The lung injury can be a manifestation of an inflammatory response and can be characterized by severe hypoxemia and a substantial reduction in pulmonary compliance due to diffuse alveolar damage, neutrophilic inflammation, and protein-rich edema in the lungs. A consequence of this damage is edema and reduced blood oxygen levels, as the affected lungs are less able to effectively transfer oxygen to the bloodstream and to remove carbon dioxide from it.

Surprisingly, it has been found that the compounds of the present invention increase rheumatoid factor (RF) production from neutrophils. Even though the neutrophils themselves are harmful, the RF factor increase is a good thing because it helps the tissue to recover. Neutrophils which are the most abundant leukocytes in the circulatory system, are present in acute lung injury. Although they play an important role in the immune system and the immune response, they contribute to inflammation-related tissue damage, because of their natural functions of phagocytosis, enzyme release, and the release of reactive oxygen species, which is generally believed to exacerbate tissue damage. However, previously it had been shown that increased reactive oxygen species (ROS) production from neutrophils by MAP3K2 and/or MAP3K3 inhibition can protect the lung during acute injury. See WO 2018/195084, to Wu et al., published Oct. 25, 2018, and Yuan, Q. et al. "Pazopanib ameliorates acute lung injuries via inhibition of MAP2K2 and MPA3K3", Science Translational Medicine, 13, eabc2499, published Apr. 28, 2021.

The inhibition of MAP3K2 and MAP3K3 can lead to an increase in ROS production in neutrophils to attenuate lung injury. The protein kinase inhibitor, pazopanib, a small-molecule anticancer drug can inhibit MAP3K2/3 and elevates ROS levels. A possible mechanism of action is that the ROS released can be converted to hydrogen peroxide, which can be protective in pulmonary vasculature integrity, thereby reducing tissue permeability and edema from lung injury. There thus seems to be a delicate balance to release enough ROS to activate protective Akt (i.e. protein kinase) phosphorylation but not enough to cause irreversible damage.

In some embodiments, a lung injury may involve edema or pulmonary edema. In some embodiments, methods of treatment using a MAP3K2/MAP3K3 inhibitor may reduce, improve, treat, or ameliorate edema or pulmonary edema. In some embodiments, a lung injury may involve increased pulmonary permeability. In some embodiments, methods of treatment using a MAP3K2/MAP3K3 inhibitor may reduce, improve, treat, or ameliorate edema or pulmonary permeability. In some embodiments, a lung injury may involve reduced pulmonary barrier function and/or reduced pulmonary barrier cell survival. In some embodiments, methods of treatment using a MAP3K2/MAP3K3 inhibitor may increase, improve, treat, or ameliorate pulmonary barrier function and/or pulmonary barrier cell survival.

MAP3K2/MAP3K3 Inhibitors

The present invention utilizes a therapeutically effective amount of a compound capable of inhibiting MAP3K2/MAP3K3, or a pharmaceutically acceptable salt, solvate, ester, or prodrug thereof for administration for treating or preventing lung injuries associated with a viral infection, such as those due to, associated with, or caused by a coronavirus infection.

MAP3K2 and MAP3K3 are two highly conserved members of the MEK kinase (MEKK) subgroup of the MAP3K superfamily. These enzymes contain a kinase domain in the C terminus and a PB1 domain near the N terminus. The kinase domains of MAP3K2 and MAP3K3 share 94% sequence identity, and these two kinases are expected to share substrates. Transient expression of the kinases in vitro leads to their auto-activation and activation of ERK1 and ERK2, p38, JNK, and ERK5. In mice, these kinases are involved in cardiovascular development, lymphocyte differentiation and NF-kappaB regulation.

MAP3K2—Mitogen-activated protein kinase 2 is an enzyme that in humans is encoded by the MAP3K2 gene. This kinase preferentially activates other kinases involved in the MAP kinase signaling pathway. This kinase has been shown to directly phosphorylate and activate IkappaB kinases, and thus plays a role in NF-kappa B signaling pathway. This kinase has also been found to bind and activate protein kinase C-related kinase 2, which suggests its involvement in a regulated signaling process.

MAP3K3—Mitogen-activated protein kinase 3 is an enzyme that in humans is encoded by the MAP3K3 gene, which is located on the long arm of chromosome 17 (17q23.3).] This gene product is a 626-amino acid polypeptide.

Coronaviruses are a group of related RNA viruses that cause diseases in mammals and birds. In humans, these viruses cause respiratory tract infections that can range from mild to lethal. By late 2020 to early 2021, several vaccines were given FDA Emergency Use Authorization and one treatment, remdesivir, is FDA approved. Other known treatments include convalescent plasma, and biologics such as recombinant antibodies.

Coronaviruses contain a positive-sense single-stranded RNA genome and a nucleocapsid of helical symmetry in a protein shell. The virus has spiked projections which in electron micrographs gives the virus an image analogous to that of the sun and its corona.

It has been found in the present invention that protein kinase inhibitors having MAP3K2/MAP3K3 inhibition activity can be useful for treating and preventing coronavirus infections, and more specifically for treating or preventing lung injury due to or associated with the infection, such as acute lung injury (ALI), lung fibrosis, and acute respiratory distress syndrome (ARDS). Compounds in this class are generally useful as anticancer agents. Examples of these compounds include, pazopanib or nintedanib, or a pharmaceutically acceptable salt, solvate, or prodrug thereof.

However, based on the prescribing information and label warnings for compounds, such as pazopanib, one of ordinary skill in the art might not have been motivated to select them for the treatment and prevention of coronavirus infections, nor for treating or preventing associated lung injury. This information would seem to teach away from the present invention to use pazopanib, and also other active compounds that are protein kinase inhibitors or that have the potential for MAP3K2/MAP3K3 inhibition.

For example, for pazopanib there is the warning that the drug "may cause lung problems that may lead to death" and the patient instructions to "[t]ell your health care provider right away if you develop a cough that will not go away or have shortness of breath." This warning would seem to teach away from the present invention to use pazopanib, or even other active compounds that are protein kinase inhibitors or that have the potential for MAP3K2/MAP3K3 inhibition. Additional warnings include "[s]erious infections" and patient instructions to "[c]all your health care provider if you experience fever; cold symptoms, such as runny nose or a sore throat that does not go away; flu symptoms, such as cough, feeling tired, and body aches . . . " Reported side effects include "trouble breathing".

Other warnings provided for pazopanib include the following:

"Interstitial Lung Disease (ILD)/Pneumonitis: ILD/pneumonitis, which can be fatal, has been reported in 0.1% of patients in the clinical trials . . . Monitor patients for ILD/pneumonitis, and discontinue . . . if symptoms of ILD or pneumonitis develop."

"Infection: Serious infections (with or without neutropenia), some with fatal outcomes, have been reported. Monitor for signs and symptoms, and treat active infection promptly. Consider interruption or discontinuation."

"Pneumothorax [i.e., lung collapse]: [It has been reported that [t]wo of 290 patients treated . . . and no patients on the placebo arm in the randomized RCC trial developed a pneumothorax. In the randomized STS trial, pneumothorax occurred in 3% (8/240) of patients treated . . . and in no patients on the placebo arm.

See the HIGHLIGHTS OF PRESCRIBING INFORMATION, VOTRIENT, May 2017; and www.hcp.novartis.com/products/votrient/?site=VRT-1218078GK100252&source=01030&gclid=EAIaIQobChMI4obj5KvD6QIVkIbACh00 EAS 4EAAYASAAEgKnRvD_BwE&gclsrc=aw.ds.

Examples of MAP3K2/MAP3K3 inhibitors useful herein include those selected from the group consisting of pazopanib or nintedanib, combinations thereof, or a pharmaceutically acceptable salt, solvate, ester, or prodrug thereof.

See U.S. Pat. No. 8,114,885, to Boloor et al., issued Feb. 14, 2012; U.S. Pat. No. 7,858,626, to Boloor et al., issued Dec. 28, 2010; U.S. Pat. No. 7,262,203, to Boloor et al., issued Aug. 28, 2007; U.S. Pat. No. 7,119,093, to Roth et al., issued Oct. 10, 2006; U.S. Pat. No. 7,105,530; to Boloor et al., issued Sep. 12, 2006; U.S. Pat. No. 6,762,180, to Roth et al., issued Jul. 13, 2004.

Pazopanib

The present invention utilizes a therapeutically effective amount of the MAP3K2/MAP3K3 inhibitor pazopanib, or a pharmaceutically acceptable salt, ester, solvate, or prodrug thereof, and also a pharmaceutically acceptable carrier, for treating or preventing lung injury due to or associated with an infection such as a coronavirus infection.

The structure of pazopanib has a pyrimidine moiety. Pazopanib is used as its hydrochloride salt for treatment of kidney cancer. It also has a role as an antineoplastic agent, a tyrosine kinase inhibitor, a vascular endothelial growth factor receptor antagonist and an angiogenesis modulating agent. Pazopanib is a member of indazoles, an aminopyrimidine and a sulfonamide and is a conjugate base of a pazopanib(1+).

Pazopanib corresponds to the following chemical structure:

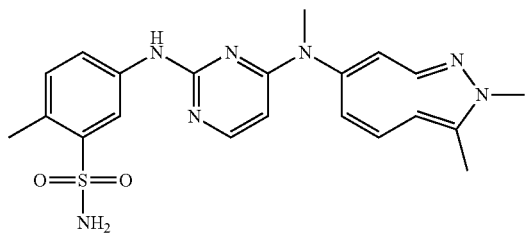

Pazopanib

Pazopanib has the IUPAC name 5-({4-[(2,3-Dimethyl-2H-indazol-6-yl)methylamino]pyrimidin-2-yl}amino)-2-methylbenzenesulfonamide and corresponds to the CAS Registry Number 444731-52-6 and ChemSpider Number 9700526. Pazopanib has the molecular formula $C_{21}H_{23}N_7O_2S$ and has a molecular weight (molar mass) of 437.5 g/mol. Pazopanib is usually delivered as the hydrochloride salt and has a molecular weight (i.e. a molar mass) for the hydrochloride salt of 1473.977 grams/mole. Therefore, 216.7 mg of pazopanib hydrochloride would be equivalent to 200 mg of pazopanib. Note that these molecular weight values will vary slightly depending on what atomic weight values are used for the calculations. Pazopanib is reported to have a half-life of 30.9-31.9 hours, a bioavailability of 14-21%, and protein binding of >99.5%.

Pazopanib was originally identified as a small molecule inhibitor of multiple protein tyrosine kinases with potential antineoplastic activity. Pazopanib selectively inhibits vascular endothelial growth factor receptors (VEGFR)-1, -2 and -3, c-kit and platelet derived growth factor receptor (PDGF-R), which may result in inhibition of angiogenesis in tumors in which these receptors are upregulated. It is used in the therapy of advanced renal cell carcinoma and soft tissue sarcomas. Pazopanib therapy is commonly associated with transient elevations in serum aminotransferase during therapy and has been linked to rare, but occasionally severe and even fatal cases of clinically apparent acute liver injury. Pazopanib is known by the trade name Votrient® and is marketed by Novartis, where it is available as a 200 mg oral tablet. Other code names associated with pazopanib include GW-786034 and UNII-7RN5DR86CK. For cancer therapy, Votrient is administered once daily without food (at least 1 hour before or 2 hours after a meal) once daily at a dose of 800 mg.

Pharmaceutically acceptable salts, esters, solvates, and prodrugs of pazopanib are useful for the methods and compositions of the present invention. As used herein, "pharmaceutically acceptable salts, esters, solvates and prodrugs" refer to derivatives of pazopanib. Examples of pharmaceutically acceptable salts include, but are not limited to, the hydrochloride salt, the hydrobromide salt, the hydroiodide salt, the hydrogen sulfate salt. As described above, the hydrochloride salt of pazopanib is currently marketed.

The pharmaceutically acceptable salts, esters, and prodrugs of pazopanib can be prepared from the parent compound by conventional chemical methods. Generally, the salts can be prepared by reacting the free base form of the compound with a stoichiometric amount of the appropriate strong acid in water or in an organic solvent, or in a mixture of the two; generally, non-aqueous media like ether, ethyl acetate, ethanol, isopropanol, or acetonitrile are preferred.

The prodrugs of pazopanib can be prepared using convention chemical methods, depending on the prodrug chosen. A prodrug is a medication or compound that, after administration, is metabolized (i.e., converted within the body) into a pharmacologically active drug. Prodrugs can be designed to improve bioavailability when a drug itself is poorly absorbed from the gastrointestinal tract. Prodrugs are intended to include covalently bonded carriers that release an active parent drug of the present invention in vivo when such prodrug is administered.

Nintedanib

The present invention utilizes a therapeutically effective amount of nintedanib, or a pharmaceutically acceptable salt, ester, solvate, or prodrug thereof, and also a pharmaceutically acceptable carrier, for treating or preventing lung injury due to or associated with a viral infection, such as a coronavirus infection. Nintedanib is a tyrosine kinase inhibitor, and the present invention provides evidence for its use as a MAP3K2/MAP3K3 inhibitor.

The structure of nintedanib has an oxo-indole. Nintedanib is usually administered in oral form as its ethanesulfonic acid salt, i.e. the esylate. Nintedanib is sold under the brand names Ofev and Vargatef, and is marketed by Boehringer Ingelheim Pharmaceuticals, Inc. Nintedanib is prescribed for the treatment of idiopathic pulmonary fibrosis and along with other medications for some types of non-small-cell lung cancer.

Nintedanib corresponds to the following chemical structure:

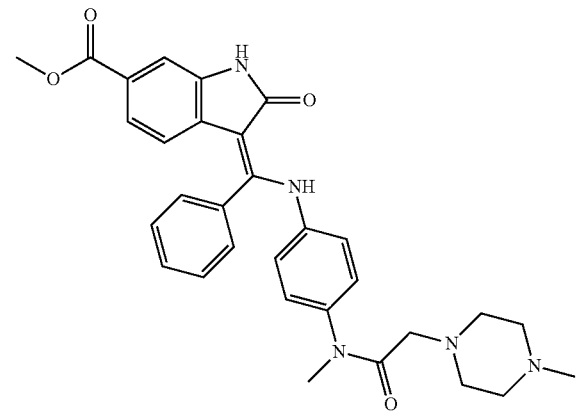

Nintedanib

Nintedanib has the IUPAC name Methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate and corresponds to the CAS Registry Number 656247-17-5 and ChemSpider Number 7985471. Nintedanib has the molecular formula $C_{31}H_{33}N_5O_4$ and has a molecular weight (molar mass) of 539.6248 g/mol. Note that the molecular weight value will vary slightly depending on what atomic weight values are used for the calculations. Nintedanib is reported to have an elimination half-life of 10-15 hours, a bioavailability of 4.7%, and protein binding of 97.8%.

Pharmaceutically acceptable salts, solvates, and prodrugs of nintedanib are useful for the methods and compositions of the present invention. As used herein, "pharmaceutically acceptable salts, solvates and prodrugs" refer to derivatives of nintedanib. Examples of pharmaceutically acceptable salts include, but are not limited to, the hydrochloride salt, the hydrobromide salt, the hydroiodide salt, the hydrogen sulfate salt. As described above, the ethane sulfonic acid salt of nintedanib is currently marketed.

The pharmaceutically acceptable salts and prodrugs of nintedanib can be prepared from the parent compound by conventional chemical methods. Generally, the salts can be prepared by reacting the free base form of the compound with a stoichiometric amount of the appropriate acid in water or in an organic solvent, or in a mixture of the two; generally, non-aqueous media like ether, ethyl acetate, ethanol, isopropanol, or acetonitrile are preferred.

The prodrugs of nintedanib can be prepared using convention chemical methods, depending on the prodrug chosen. A prodrug is a medication or compound that, after administration, is metabolized (i.e., converted within the body) into a pharmacologically active drug. Prodrugs can be designed to improve bioavailability when a drug itself is poorly absorbed from the gastrointestinal tract. Prodrugs are intended to include covalently bonded carriers that release an active parent drug of the present invention in vivo when such prodrug is administered.

Dosages and Treatment Regimens

In some embodiments, the compositions comprises from about 1 to about 1000 mg, or from about 10 to about 1000 mg, or from about 50 to about 1000 mg, or from about 100 to about 1000 mg, or from about 100 to about 900 mg, or from about 100 to about 800 mg, or from about 200 to about 800 mg, or from about 200 to about 700 mg, or from about 200 to about 600 mg, or from about 200 to about 500 mg, or from about 200 to about 400 mg, or from about 200 to about 300 mg per unit dosage of the compound capable of inhibiting MAP3K2/MAP3K3 based on the active moiety of the compound. In some embodiments, the compositions can comprise about 1 mg, or about 5 mg, or about 10 mg, or about 25 mg or about 50 mg, or about 100 mg, or about 150 mg, or about 200 mg, or about 250 mg or about 300 mg, or about 350 mg or about 400 mg, or about 450 mg, or about 500 mg, or about 550 mg or about 600 mg, or about 650 mg, or about 700 mg, or about 800 mg, or about 900 mg, or about 1000 mg per unit dosage of the compound capable of inhibiting MAP3K2/MAP3K3 based on the active moiety of the compound.

In some embodiments, a dosing range for the compound capable of inhibiting MAP3K2/MAP3K3 based on the active moiety of the compound is from about 0.01 mg/kg to about 1000 mg/kg of body weight/per day of the subject.

The dosage can be varied to achieve an amount of the active ingredient that is effective for obtaining the desired therapeutic effect.

The target indication of the invention composition is related to methods of treating or preventing lung injury due to or associated with coronavirus infections. The compositions of the present invention can be administered according to a variety of regimens.

For example, the composition is administered from the group consisting of about four times per day, about three times per day, about two times per day, about one time per day, about one time every other day, about two times per week, and about one time per week. Furthermore, the composition can be administered about one time per day, or about two times per day, or about three times per day, or about four times per day.

The composition is administered until the infection is treated. Periods of administration include those selected from the group consisting of about 1 day to about 30 days [or about one month], about 1 day to about 14 days, about 1 day to about 10 days, about 1 day to about 1 week (7 days), about 1 day to about 5 days, or about 1 day to about 3 days.

It is also desirable to achieve appropriate pharmacokinetic and/or pharmacodynamic properties. The methods and compositions in some embodiments demonstrate at least one of the following pharmacokinetic parameters in the patient: an AUC of about 1,037 mcg*h/mL or a Cmax of about 58.1 mcg/mL (equivalent to about 132 μM) for the compound capable of inhibiting MAP3K2/MAP3K3.

Combination Therapies

In other embodiments, the patient or subject can be administered at least one additional active agent for treating, preventing or reducing the severity of the lung injury, or to treat, prevent, or reduce the severity of the viral infection or other disease manifestations or symptoms.

In some embodiment, the compositions and methods of the present invention can be provided in combination with the anti-viral agent remdesivir. Remdesivir is an investigational broad-spectrum antiviral medication developed by Gilead Sciences, Inc. that is currently being evaluated as a treatment for COVID-19. It has been authorized for emergency use in the United States and approved for use in Japan. It has the IUPAC chemical name (2S)-2-{(2R,3S,4R,5R)-[5-(4-Aminopyrrolo[2,1-f][1,2,4]triazin-7-yl)-5-cyano-3,4-dihydroxy-tetrahydro-furan-2-ylmethoxy]phenoxy-(S)-phosphorylamino}propionic acid 2-ethyl-butyl ester, CAS Registry Number 1809249-37-3 and ChemSpider Number 58827832. Remdesivir corresponds to the chemical formula $C_{27}H_{35}N_6O_8P$, and has a molar mass of 602.585 g/mol.

Formulations

In the present invention other optional ingredients may also be incorporated into the nasal delivery system provided they do not interfere with the action of the drug or significantly decrease the absorption of the drug across the nasal mucosa. Such ingredients can include, for example, pharmaceutically acceptable excipients and preservatives. The excipients that can be used in accordance with the present invention include, for example, bio-adhesives and/or swelling/thickening agents.

In the present invention, any other suitable absorption enhancers as known in the art may also be used.

Preservatives can also be added to the present compositions. Suitable preservatives that can be used with the present compositions include, for example, benzyl alcohol, parabens, thimerosal, chlorobutanol and benzalkonium, with benzalkonium chloride being preferred. Typically, the preservative will be present in the present compositions in a concentration of up to about 2% by weight. The exact concentration of the preservative, however, will vary depending upon the intended use and can be easily ascertained by one skilled in the art.

The absorption enhancing agent includes (i) a surfactant; (ii) a bile salt (including sodium taurocholate); (iii) a phospholipid additive, mixed micelle, or liposome; (iv) an alcohol (including a polyol as discussed above, for example, propylene glycol or polyethylene glycol such as PEG 3000, etc.); (v) an enamine; (vi) a nitric oxide donor compound; (vii) a long-chain amphipathic molecule; (viii) a small hydrophobic uptake enhancer; (ix) sodium or a salicylic acid derivative; (x) a glycerol ester of acetoacetic acid; (xi) a cyclodextrin or cyclodextrin derivative; (xii) a medium-chain or short-chain (e.g. Cl to C 12) fatty acid; and (xiii) a chelating agent; (xiv) an amino acid or salt thereof; and (xv) an N-acetylamino acid or salt thereof.

Solubility enhancers may increase the concentration of the drug or pharmaceutically acceptable salt thereof in the formulation. Useful solubility enhancers include, e.g., alcohols and polyalcohols.

An isotonizing agent may improve the tolerance of the formulation in a nasal cavity. A common isotonizing agent is NaCl. Preferably, when the formulation is an isotonic intranasal dosage formulation, it includes about 0.9% NaCl (v/v) in the aqueous portion of the liquid carrier.

The thickeners may improve the overall viscosity of the composition, preferably to values close to those of the nasal mucosa. Suitable thickeners include methylcellulose, carboxymethylcellulose, polyvinylpyrrolidone, sodium alginate, hydroxypropylmethylcellulose, and chitosan.

A humectant or anti-irritant improves the tolerability of the composition in repeated applications. Suitable compounds include, e.g. glycerol, tocopherol, mineral oils, and chitosan.

Various additional ingredients can be used in the compositions of the present invention. The compositions can comprise one or more further ingredients selected from a preservative, an antioxidant, an emulsifier, a surfactant or wetting agent, an emollient, a film-forming agent, or a viscosity modifying agent. These components can be employed and used at levels appropriate for the formulation based on the knowledge of one with ordinary skill in the pharmaceutical and formulation arts. The amounts could range from under 1 percent by weight to up to 90 percent or even over 99 percent by weight.

In another aspect, suitable propellants can be used for dispensing the product when in the form of a liquid or powder for delivery from a spray device or nebulizer.

In one aspect, a preservative can be included. In another aspect, an antioxidant can be included. In another aspect, an emulsifier can be included. In another aspect, an emollient can be included. In another aspect, a viscosity modifying agent can be included. In another aspect, a surfactant or wetting agent can be included. In another aspect, a film forming agent can be included. In another aspect, the pharmaceutical composition is in the form selected from the group consisting of a gel, ointment, lotion, emulsion, cream, liquid, spray, suspension, jelly, foam, mousse, paste, tape, dispersion, aerosol. These components can be employed and used at levels appropriate for the formulation based on the knowledge of one with ordinary skill in the pharmaceutical and formulation arts.

In another aspect, the at least one preservative can be selected from the group consisting of parabens (including butylparabens, ethylparabens, methylparabens, and propylparabens), acetone sodium bisulfite, alcohol, benzalkonium chloride, benzethonium chloride, benzoic acid, benzyl alcohol, boric acid, bronopol, butylated hydroxyanisole, butylene glycol, calcium acetate, calcium chloride, calcium lactate, cetrimide, cetylpyridinium chloride, chlorhexidine, chlorobutanol, chlorocresol, chloroxylenol, cresol, edetic acid, glycerin, hexetidine, imidurea, isopropyl alcohol, monothioglycerol, pentetic acid, phenol, phenoxyethanol, phenylethyl alcohol, phenylmercuric acetate, phenylmercuric borate, phenylmercuric nitrate, potassium benzoate, potassium metabisulfite, potassium nitrate, potassium sorbate, propionic acid, propyl gallate, propylene glycol, propylparaben sodium, sodium acetate, sodium benzoate, sodium borate, sodium lactate, sodium metabisulfite, sodium propionate, sodium sulfite, sorbic acid, sulfur dioxide, thimerosal, zinc oxide, and N-acetylcysteine, or a combination thereof. These components can be employed and used at levels appropriate for the formulation based on the knowledge of one with ordinary skill in the pharmaceutical and formulation arts. The amounts could range from under 1 percent by weight to up to 30 percent by weight.

In another aspect, the at least one antioxidant can be selected from the group consisting of acetone sodium bisulfite, alpha tocopherol, ascorbic add, ascorbyl palmitate, butylated hydroxyanisole, butylated hydroxytoluene, citric acid monohydrate, dodecyl gallate, erythorbic acid, fumaric acid, malic acid, mannitol, sorbitol, monothioglycerol, octyl gallate, potassium metabisulfite, propionic acid, propyl gallate, sodium ascorbate, sodium formaldehyde sulfoxylate, sodium metabisulfite, sodium sulfite, sodium thiosulfate, sulfur dioxide, thymol, vitamin E polyethylene glycol succinate, and N-acetylcysteine, or a combination thereof. These components can be employed and used at levels appropriate for the formulation based on the knowledge of one with ordinary skill in the pharmaceutical and formulation arts. The amounts could range from under 1 percent by weight to up to 30 percent by weight.

In another aspect, the at least one emulsifier can be selected from the group consisting of acacia, agar, ammonium alginate, calcium alginate, carbomer, carboxymethylcellulose sodium, cetostearyl alcohol, cetyl alcohol, cholesterol, diethanolamine, glyceryl monooleate, glyceryl monostearate, hectorite, hydroxypropyl cellulose, hydroxypropyl starch, hypromellose, lanolin, lanolin alcohols, lauric acid, lecithin, linoleic acid, magnesium oxide, medium-chain triglycerides, methylcellulose, mineral oil, monoethanolamine, myristic acid, octyldodecanol, oleic acid, oleyl alcohol, palm oil, palmitic acid, pectin, phospholipids, poloxamer, polycarbophil, polyoxyethylene alkyl ethers, polyoxyethylene castor oil derivatives, polyoxyethylene sorbitan fatty acid esters, polyoxyethylene stearates, polyoxyl 15 hydroxystearate, polyoxyglycerides, potassium alginate, propylene glycol alginate, propylene glycol dilaurate, propylene glycol monolaurate, saponite, sodium borate, sodium citrate dehydrate, sodium lactate, sodium lauryl sulfate, sodium stearate, sorbitan esters, starch, stearic acid, sucrose stearate, tragacanth, triethanolamine, tromethamine, vitamin E polyethylene glycol succinate, wax, and xanthan gum, or a combination thereof. These components can be employed and used at levels appropriate for the formulation based on the knowledge of one with ordinary skill in the pharmaceutical and formulation arts. The amounts could range from under 1 percent by weight to up to 30 percent by weight.

In another aspect, the at least one emollient can be selected from the group consisting of almond oil, aluminum monostearate, butyl stearate, canola oil, castor oil, cetostearyl alcohol, cetyl alcohol, cetyl palmitate, cholesterol, coconut oil, cyclomethicone, decyl oleate, diethyl sebacate, dimethicone, ethylene glycol stearates, glycerin, glyceryl monooleate, glyceryl monostearate, isopropyl isostearate, isopropyl myristate, isopropyl palmitate, lanolin, lanolin alcohols, lecithin, mineral oil, myristyl alcohol, octyldodecanol, oleyl alcohol, palm kernel oil, palm oil, petrolatum, polyoxyethylene sorbitan fatty acid esters, propylene glycol dilaurate, propylene glycol monolaurate, safflower oil, squalene, sunflower oil, tricaprylin, triolein, wax, xylitol, zinc acetate, or a combination thereof. These components can be employed and used at levels appropriate for the formulation based on the knowledge of one with ordinary skill in the pharmaceutical and formulation arts. The amounts could range from under 1 percent by weight to up to 60 percent by weight.

In another aspect, the at least one viscosity modifying agent can be selected from the group consisting of acacia, agar, alginic acid, aluminum monostearate, ammonium alginate, attapulgite, bentonite, calcium alginate, calcium lactate, carbomer, carboxymethylcellulose calcium, carboxymethylcellulose sodium, carrageenan, cellulose, ceratonia, ceresin, cetostearyl alcohol, cetyl palmitate, chitosan, colloidal silicon dioxide, corn syrup solids, cyclomethicone, ethylcellulose, gelatin, glyceryl behenate, guar gum, hectorite, hydrophobic colloidal silica, hydroxyethyl cellulose, hydroxyethylmethyl cellulose, hydroxypropyl cellulose, hydroxypropyl starch, hypromellose, magnesium aluminum silicate, maltodextrin, methylcellulose, myristyl alcohol, octyldodecanol, palm oil, pectin, polycarbophil, polydextrose, polyethylene oxide, polyoxyethylene alkyl ethers, polyvinyl alcohol, potassium alginate, propylene glycol alginate, pullulan, saponite, sodium alginate, starch, sucrose, sugar, sulfobutylether β-cyclodextrin, tragacanth, trehalose, and xanthan gum, or a combination thereof. These components can be employed and used at levels appropriate for the formulation based on the knowledge of one with ordinary skill in the pharmaceutical and formulation arts. The amounts could range from under 1 percent by weight to up to 60 percent.

In another aspect, the at least one film forming agent can be selected from the group consisting of ammonium alginate, chitosan, colophony, copovidone, ethylene glycol and vinyl alcohol grafted copolymer, gelatin, hydroxypropyl cellulose, hypromellose, hypromellose acetate succinate, polymethacrylates, poly(methyl vinyl ether/maleic anhydride), polyvinyl acetate dispersion, polyvinyl acetate phthalate, polyvinyl alcohol, povidone, pullulan, pyroxylin, and shellac, or a combination thereof. These components can be employed and used at levels appropriate for the formulation based on the knowledge of one with ordinary skill in the pharmaceutical and formulation arts. The amounts could range from under 1 percent by weight to up to 90 percent or even over 99 percent by weight.

In another aspect, the at least one surfactant or wetting agent can be selected from the group consisting of docusate sodium, phospholipids, sodium lauryl sulfate, benzalkonium chloride, cetrimide, cetylpyridinium chloride, alpha tocopherol, glyceryl monooleate, myristyl alcohol, poloxamer, polyoxyethylene alkyl ethers, polyoxyethylene castor oil derivatives, polyoxyethylene sorbitan fatty acid esters, polyoxyethylene stearates, polyoxyl 15 hydroxystearate, polyoxyglycerides, propylene glycol dilaurate, propylene glycol monolaurate, sorbitan esters, sucrose stearate, tricaprylin, and vitamin E polyethylene glycol succinate, or a combination thereof. These components can be employed and used at levels appropriate for the formulation based on the knowledge of one with ordinary skill in the pharmaceutical and formulation arts. The amounts could range from under 1 percent by weight to up to 30 percent by weight.

In another aspect, a buffering agent can be included. In another aspect, an emollient can be included. In another aspect, an emulsifying agent can be included. In another aspect, an emulsion stabilizing agent can be included. In another aspect, a gelling agent can be included. In another aspect, a humectant can be included. In another aspect, an ointment base or oleaginous vehicle can be included. In another aspect, a suspending agent can be included. In another aspect an acidulant can be included. In another aspect, an alkalizing agent can be included. In another aspect, a bioadhesive material can be included. In another aspect, a colorant can be included. In another aspect, a microencapsulating agent can be included. In another aspect, a stiffening agent can be included. These components can be employed and used at levels appropriate for the formulation based on the knowledge of one with ordinary skill in the pharmaceutical and formulation arts. The amounts could range from under 1 percent by weight to up to 90 percent or even over 99 by weight.

One of ordinary skill in the pharmaceutical and formulation arts can determine the appropriate levels of the essential and optional components of the compositions of the present invention.

The compositions of the present invention can be in a variety of forms including oral and intravenous forms, and also parenteral forms and compositions for injection. However, because delivery to the lungs is highly desirable the following routes of administration are preferred: nasal, inhalation (i.e. respiratory), intratracheal, intrapulmonary, and intrabronchial.

The compositions can be in the form of liquids, suspensions or dry powders. These compositions can be delivered into the lungs via a nebulizer or atomizer. The present invention also contemplates devices for spraying the compositions and kits comprising such a delivery device and instructions for use.

Methods of preparing the compositions are also intended as part of the present invention and would be apparent to one of ordinary skill in the pharmaceutical and formulation arts using standard formulation and mixing techniques.

Methods of Treatment

The present invention utilizes a therapeutically effective amount of a compound having MAP3K2/MAP3K3 inhibition activity, or a pharmaceutically acceptable salt thereof and a pharmaceutically acceptable carrier for treating or preventing lung injury due to or associated with an infection such as a coronavirus infection.

The methods may comprise administration to or into the lung of a patient in need thereof. The methods may also comprise any other administration route that provides a therapeutically effective and sufficient concentration of the compound in the lungs and/or systemically, such as oral, oropharyngeal, parenteral, nasal, respiratory (inhalation), intraperitoneal, intrapleural, intravenous, lanyngeal, oropharyngeal, topical, transdermal, transmucosal intratracheal, intrapulmonary, and intrabronchial.

Various dosing regimens can be prescribed and used based on the skill and knowledge of the physician or other practitioner. In some embodiments, a unit dosage of the composition, as described herein can be applied at least once daily. In other embodiments, a unit dosage of the composition can be applied at least twice daily, or at least once weekly, or at least twice weekly. Based on the pharmacokinetic and pharmacodynamic parameters of the active ingredient, the dosing amount and regimen can be appropriately varied.

Therapy can be continued in the judgment of the physician or practitioner until the desired therapeutic benefit is achieved. In some instances, it can be desirable to continue long term or chronic therapy.

The therapy of the present invention is especially important for those patients that are hospitalized and critically ill, particularly those in intensive care units. The invention is useful for those patients on ventilators and respirators.

In lung injury, a number of factors can be involved. The methods of the present invention provide a means for reducing edema, and in maintain and increasing blood oxygen levels in those patients that have been compromised due to the lung injury. The present methods also provide a means to increase RF (rheumatoid factor) production from neutrophils. These factors help damaged tissue to recover. Neutrophils within synovial fluid are activated by soluble immune complexes (RF, ACPA) that induce neutrophil degranulation and release of reactive oxygen species (ROS) and proteases, which lead to degradation of hyaluronic acid and activation of cytokines.

The compositions can be administered by those routes to most effectively have it get into the lungs. The compositions can be administered via aerosol generating devices such as nebulizers. The compositions can be part of a kit for therapeutic treatment. The kits can comprise an applicator device and also instructional material for using it.

Kits for Providing Compositions and Treatment

The present invention also includes kits for providing the compositions and methods of treatment. These kits comprise the pharmaceutical composition, instruction materials and prescribing information, and for certain modes of administration a spray device or nebulizer. In further embodiments, the kits can comprise additional active ingredients for treating, preventing or reducing the severity of the lung injury or for managing other symptoms or aspects of the viral infection. The kits can also provide personal protective equipment such as face masks, disposable gloves, and disposable protective garments for healthcare professionals and other workers involved with administering the treatment to the patient.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Example 1: Investigation of Pazopanib on Lung Injuries

We investigated the effects of the FDA-approved anti-cancer drug pazopanib on lung injuries in a mouse coronavirus-induced pneumonitis mode We have strong data to show that pazopanib is a substrate specific inhibitor of MAP3K2 and 3 and that inhibition of these two protein kinases ameliorates lung injury, which is believed to be a major contributor of death associated with COVID-19. To provide further confidence and justification for carrying out human study of the drug on COVID-19 patients, we propose to investigate the effects of pazopanib in a mouse model infected with coronavirus MHV-1, which exhibit lung injury phenotypes similarly to those caused by SARS-CoV.

The current COVID-19 pandemic is caused by a novel coronavirus, designated as severe acute respiratory syndrome coronavirus 2 (SARS-CoV-2). The disease causes death of about 2% cases probably due to massive alveolar damage and progressive respiratory failure. Published pulmonary pathology and radiological reports of COVID-19 and previous SARS-CoV or Middle Eastern respiratory syndrome (MERS) provide clear association of the disease with acute respiratory distress syndrome (ARDS) [1-4].

ARDS is a severe form of acute lung injury (ALI), which is caused by direct or indirect insults to the lung [5, 6]. In case of COVID-19, lung injury is likely caused by both direct and indirect means. SARS-CoV has been shown to cause necrosis of lung epithelial cells (direct insult). In addition, strong inflammatory responses elicited by the viral infection should also cause lung injury (indirect insult). In addition to viral infection, there are many other causes for ALI/ARDS, including bacterial infection, gastric acid aspiration, and trauma. The incidence of ALI/ARDS is reported to be around 200,000 per year in the US (excluding COVID-19) with a mortality rate of around 40% [5]. Currently there are no pharmacological interventions for the diseases. Care of these conditions is largely dependent on supportive measures [7, 8]. This probably contributes to the high fatality rate of COVID-19 and high demand of respirators.

In our study of the functional roles of two protein kinases MAP3K2 and 3, we inadvertently discovered that inhibition of these two kinases abates acute lung injuries in mouse models involving an unexpected beneficial effect of paracrine ROS from myeloid cells (see attached manuscript). A hallmark of ALI/ARDS is the abundant presence of neutrophils in the lungs [9]. This is also true in SARS-CoV-induced ARDS [1, 4]. We found that genetic inactivation of these two kinase homologs increased ROS production in neutrophils. In addition, the lack of these MAP3K kinases in myeloid cells attenuated lung injury manifestations and reduced mortality in both direct and indirect lung insult mouse ALI models. Mechanistically, the kinases phosphorylate the Nox2 subunit $p47^{phox}$ at Ser208 to inhibit $p47^{phox}$ interaction with $p22^{phox}$ and hence Nox2 activity. The importance of Ser208 phosphorylation was further confirmed by its knock-in mutation; hematopoietic loss of $p47^{phox}$ Ser208 phosphorylation recapitulated the effects of MAP3K2/3 loss on neutrophils and ALI. Moreover, we found that inhibition of the MAP3K-$p47^{phox}$ pathway in myeloid cells acted on both pulmonary vasculature and epithelial cells to enhance the pulmonary barrier function and protect lungs from injuries. We subsequently identified pazopanib, which is an FDA-approved drug for cancer treatment, as being a high-affinity (low nanomolar), $p47^{phox}$ substrate-specific inhibitor for MAP3K2 and 3. Pazopanib was effective in ameliorating ALI in the two mouse ALI/ARDS models in a manner dependent on these two kinases and ROS production. Given the drug has been well tolerated in clinic, pazopanib is very likely to be quickly repurposed for treating ALI/ARDS caused by SARS-Cov-2 in this COVID-19 pandemic. The test of pazopanib in a mouse coronavirus infection model that closely resembles human SARS-CoV pulmonary pathology would provide further confidence and justification for human study of this drug on COVID-19 patients.

Research Strategy

1. Establishment and verification of coronavirus induced SARS-like pulmonary disease model in mice.

De Albuquerque, et al. reported in 2006 that intranasal infection of A/J mice with the coronavirus murine hepatitis virus strain 1 (MHV-1) produced ALI/ARDS features of SARS [10]. All MHV-1-infected A/J mice developed progressive interstitial edema, neutrophil/macrophage infiltrates, and hyaline membranes, leading to death of all mice. We plan to use this model to test prophylactic and therapeutic effects of pazopanib. The A/J mice will be purchased from Charles River and MHV-1 will be purchased from ATCC (ATCC VR-261, the same sources used by De Albuquerque, et al.; Jim Macy's lab also has this strain). Viruses will be first plaque purified and then expanded in murine 17CL1 cells or NCTC clone 1469 (ATCC CCL-9.1). Supernatants are to be collected and subsequently stored at −80° C. until use. Viral titers are determined via plaque assay using the L2 cells (ATCC CCL-149) [10]. We will start with viral titration test in mice based on what was described by De Albuquerque, et al. In that report, mice were infected with 5,000 PFU intranasally, which resulted in ALI phenotypes in two days and death in 7-8 days. We will repeat the experiments with 1000, 2500, 5000, 10000 PFU. Mice survival will be monitored up to 21 days and H&E (hematoxylin and eosin) staining will be performed on lungs and livers collected at day 0, day 2 and day 6 post-MHV infection. Meanwhile, virus titers in lung, brain, liver and spleen and cytokines (IL-6, IL-10, INF-g, TNF-a and MCP-1) levels in blood and BAL (bronchoalveolar lavage) will be determined at day 0, day 2, day 4 and day 6.

Anticipated Outcomes

We expect to see A/J mice develop pulmonary pathological features of SARS including dense macrophage/neutrophil infiltrates, pulmonary edema and hyaline membranes. Cytokines levels are expected to be elevated in the lungs and blood.

2. Test the effects of pazopanib on lung injuries in coronavirus induced SARS-like pulmonary disease model.

Once the proper viral dose is determined, the effects of pazopanib will be tested in this mouse model. Based on our preliminary data for treating lung injuries induced by HCl in mice, 3 mg/kgbw for pazopanib intravenous (IV)-injection and 65 mg/kgbw for gavage delivery are best doses, so we will start from here and try different doses. Mice will be first intranasally injected with MHV-1 virus, pazopanib will be delivered to mice via IV at 3 mg/kgbw or via gavage at 65 mg/kgbw, starting from 12 hr post virus infection followed by every 24 hr delivery. Control mice will be infected with virus as well and delivered with vehicle at the same time points. Mice will be monitored daily for symptoms of disease, including ruffled fur, tremors and lack of activity. Survival rate will be examined and pulmonary permeability will be determined using FITC-Albumin as what we did in other mouse ALI model. Histological examination of lungs and livers, viral titers in different organs and cytokines measurements will be determined as what we described above (section 1). In addition, pharmacokinetics of pazopanib in blood will be determined using established LC/MS method [11]. Besides therapeutic effect, prophylactic effect of pazopanib will be evaluated as well. In this case, pazopanib will be delivered 12 hr before infection via gavage or 2 hr before infection via IV followed by every 24 hr delivery and the rest evaluation will be the same as what we planned above.

Based on the results from the acid-induced direct insult and LPS-induced indirect insult ALI models we performed, we anticipate that pazopanib treatment should have effects on pulmonary edema in this MHV-1 infection model. We hope that the drug can impact mortality rate as we have seen with acid and LPS models. And we also hope to see prophylactic effect of this drug on lung injury as what we have observed in our acid and LPS models. If any of the results is observed, the drug should be justifiable for immediate human trial.

REFERENCES

1. Tian, S., et al., *Pulmonary Pathology of Early-Phase 2019 Novel Coronavirus (COVID-19) Pneumonia in Two Patients With Lung Cancer.* J Thorac Oncol, 2020.
2. Ng, D. L., et al., *Clinicopathologic, Immunohistochemical, and Ultrastructural Findings of a Fatal Case of Middle East Respiratory Syndrome Coronavirus Infection in the United Arab Emirates*, April 2014. Am J Pathol, 2016. 186 (3): p. 652-8.
3. Ding, Y., et al., *The clinical pathology of severe acute respiratory syndrome (SARS): a report from China.* J Pathol, 2003. 200 (3): p. 282-9.
4. Xu, Z., et al., *Pathological findings of COVID-19 associated with acute respiratory distress syndrome.* The Lancet Respiratory Medicine, 2020.
5. Johnson, E. R. and M. A. Matthay, *Acute Lung Injury: Epidemiology, Pathogenesis, and Treatment.* Journal of Aerosol Medicine and Pulmonary Drug Delivery, 2010. 23 (4): p. 243-252.
6. Maca, J., et al., *Past and Present ARDS Mortality Rates: A Systematic Review.* Respir Care, 2017. 62 (1): p. 113-122.
7. Brower, R. G., et al., *Ventilation with lower tidal volumes as compared with traditional tidal volumes for acute lung injury and the acute respiratory distress syndrome.* New England Journal of Medicine, 2000. 342 (18): p. 1301-1308.
8. Weinert, C. R., C. R. Gross, and W. A. Marinelli, *Impact of randomized trial results on acute lung injury ventilator therapy in teaching hospitals.* American Journal of Respiratory and Critical Care Medicine, 2003. 167 (10): p. 1304-1309.
9. Matthay, M. A. and R. L. Zemans, *The acute respiratory distress syndrome: pathogenesis and treatment.* Annu Rev Pathol, 2011. 6: p. 147-63.
10. De Albuquerque, N., et al., *Murine hepatitis virus strain 1 produces a clinically relevant model of severe acute respiratory syndrome in A/J mice.* J Virol, 2006. 80 (21): p. 10382-94.
11. Minocha, M., V. Khurana, and A. K. Mitra, *Determination of pazopanib (GW-786034) in mouse plasma and brain tissue by liquid chromatography-tandem mass spectrometry (LC/MS-MS).* J Chromatogr B Analyt Technol Biomed Life Sci, 2012. 901: p. 85-92.

Example 2: Composition for Inhalation Delivery

The following composition is prepared using standard mixing equipment and procedures.

| Ingredient | Amount |
|---|---|
| Pazopanib hydrochloride | 100 to 800 mg/ml* |
| Water | QS to achieve the indicated levels of ingredients |

*Active amount based on hydrochloride salt

The pazopanib hydrochloride salt is suspended or dissolved in water with gentle mixing.

The composition can be packaged in a spray bottle or nebulizer for inhalation administration.

The composition is useful for treating or preventing lung injury due to or associated with a coronavirus infection.

In another embodiment, the composition of Example 1 is prepared using nintedanib esylate in place of pazopanib hydrochloride.

Example 3: Efficacy Evaluation of Three Doses of Pazopanib Hydrochloride in Mouse Coronavirus Induced Lung Injury Model Purpose:
Evaluate the efficacy of pazopanib hydrochloride composition in coronavirus (Murine Hepatitis Virus Strain 1, MHV-1) induced mouse lung injury model.
Procedure:
a. Pazopanib Composition Preparation
1. Put 3.294 ml double distilled water (ddH2O) in a small beaker with a small magnetic stir bar.
2. Weigh 1.663 g 2-Hydroxypropyl-beta-cyclodextrin (HP-b-CD).
3. Add HP-b-CD slowly into the water while stirring.
4. Keep stirring until HP-b-CD completely dissolved.
5. Transfer the HP-b-CD solution into a 15 ml tube.
6. Weigh 43 mg pazopanib hydrochloride and add it into HP-b-CD solution.
7. Vibrate the tube for 5 min followed by 30 min water bath sonication.
8. Then keep the tube in 50° C. for 30 min and pazopanib hydrochloride should be completely dissolved.
Vehicle Stock: 33.26% (332.6 mg/ml) HP-b-CD in ddH2O
Stock solution of pazopanib: 8.6 mg/ml in vehicle control

| | Vehicle Stock | Pazopanib stock |
|---|---|---|
| Vehicle control | 100 ul | 0 ul |
| 3 mg/kgbw | 93.03 ul | 6.97 ul |

* Each mouse is around 20 gbw and retro-orbital injection volume is 100 ul b. Animal Procedure
A/J mice, 8-10 weeks old, were anaesthetized by Ketamine/Xylazine (100 mg/kg and 10 mg/kg) and were kept under anesthesia during the whole procedure using Ketamine/Xylazine. After being deeply anesthetized (assessed by applying a noxious stimulus, eg toe pinch, and observing no reflex response and no change in either the rate or character of respiration), mice received an intranasal inoculation of 5000 PFU MHV-1 in 20 μl Dulbecco's modified Eagle's medium. After the administration, the mice were monitored until their breathing gradually returned to normal. Then the mice were returned to the recovery cage on the heating pad and monitored for their anesthesia status. Six hours after the virus inoculation, vehicle control or 3 mg/kgbw (mg per kg of body weight) pazopanib was delivered to mice via retro-orbital. Twenty-one hours after the virus inoculation, vehicle control or 3 mg/kgbw pazopanib was delivered to mice via retro-orbital again. After another eleven hours, the $3^{rd}$ dose of vehicle control or 3 mg/kgbw pazopanib was delivered to mice via retro-orbital as well. Fifteen hours after the 3rd dose of the drug administration, 100 μl of FITC-labeled albumin (10 mg/ml) was injected via the retro-orbital vein. Two hours after FITC-albumin injection, mice were euthanized and bronchoalveolar lavage (BAL) was collected via instilling 1 ml of phosphate-buffered saline (PBS) into the lungs, which was retrieved via a tracheal catheter. The green fluorescent of BAL was measured by the plate reader. BAL fluorescent intensities from pazopanib treated mice were normalized to the intensities from vehicle control-treated mice.

Conclusion:
As shown in FIG. 1, treatment with a pharmaceutical composition of pazopanib can significantly reduce pulmonary permeability in mouse coronavirus induced acute lung injury model when 3 doses were given at 3 mg/kgbw.

Example 4: Efficacy Evaluation of Two Doses of Pazopanib Composition in Mouse Coronavirus Induced Lung Injury Model 1. Purpose:
Evaluate the efficacy of pazopanib composition in coronavirus (Murine Hepatitis Virus Strain 1, MHV-1) induced mouse lung injury model.
2. Procedure:
a. Pazopanib Composition Preparation
1. Put 3.294 ml ddH2O in a small beaker with a small magnetic stir bar.
2. Weigh 1.663 g 2-Hydroxypropyl-beta-cyclodextrin (HP-b-CD).
3. Add HP-b-CD slowly into the water while stirring.
4. Keep stirring until HP-b-CD completely dissolved.
5. Transfer the HP-b-CD solution into a 15 ml tube.
6. Weigh 43 mg pazopanib hydrochloride and add it into HP-b-CD solution.
7. Vibrate the tube for 5 min followed by 30 min water bath sonication.
8. Then keep the tube in 50° C. for 30 min and pazopanib hydrochloride should be completely dissolved.
Vehicle Stock: 33.26% (332.6 mg/ml) HP-b-CD in ddH2O
Stock solution of pazopanib: 8.6 mg/ml in vehicle control

| | Vehicle Stock | Pazopanib stock |
|---|---|---|
| Vehicle control | 100 ul | 0 ul |
| 3 mg/kgbw | 93.03 ul | 6.97 ul |

* Each mouse is around 20 gbw and retro-orbital injection volume is 100 ul b. Animal Procedure
A/J mice, 8-10 weeks old, were anaesthetized by Ketamine/Xylazine (100 mg/kg and 10 mg/kg) and were kept under anesthesia during the whole procedure using Ketamine/Xylazine. After being deeply anesthetized (assessed by applying a noxious stimulus, eg toe pinch, and observing no reflex response and no change in either the rate or character of respiration), mice received an intranasal inoculation of 6000 PFU MHV-1 in 20 μl Dulbecco's modified Eagle's medium. After the administration, the mice were monitored until their breathing gradually returned to normal. Then the mice were returned to the recovery cage on the heating pad and monitored for their anesthesia status. Twenty-four hours after the virus inoculation, vehicle control or 3 mg/kgbw pazopanib was delivered to mice via retro-orbital. Thirty-three hours after the virus inoculation, vehicle control or 3 mg/kgbw pazopanib was delivered to mice via retro-orbital again. Sixteen hours after the $2^{nd}$ dose of the drug administration, 100 μl of FITC-labeled albumin (10 mg/ml) was injected via the retro-orbital vein. Two hours after FITC-album in injection, mice were euthanized and bronchoalveolar lavage (BAL) was collected via instilling 1 ml of PBS into the lungs, which was retrieved via a tracheal catheter. The green fluorescent of BAL was measured by the plate reader. BAL fluorescent intensities from pazopanib treated mice were normalized to the intensities from vehicle control-treated mice.

Figure 2:
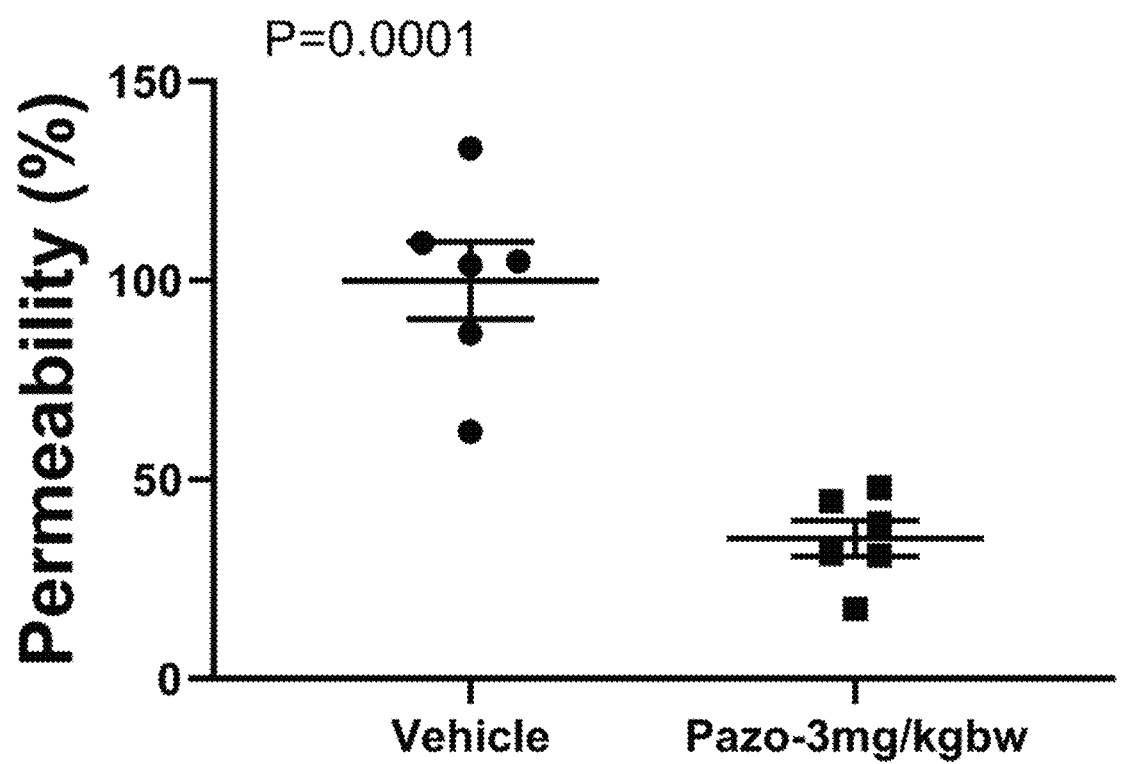
FIG. 2 shows pulmonary permeability in a mouse coronavirus induced acute lung injury model with two doses of a MAP3K2/MAP3K3 inhibitor after virus inoculation.
Figure 3:
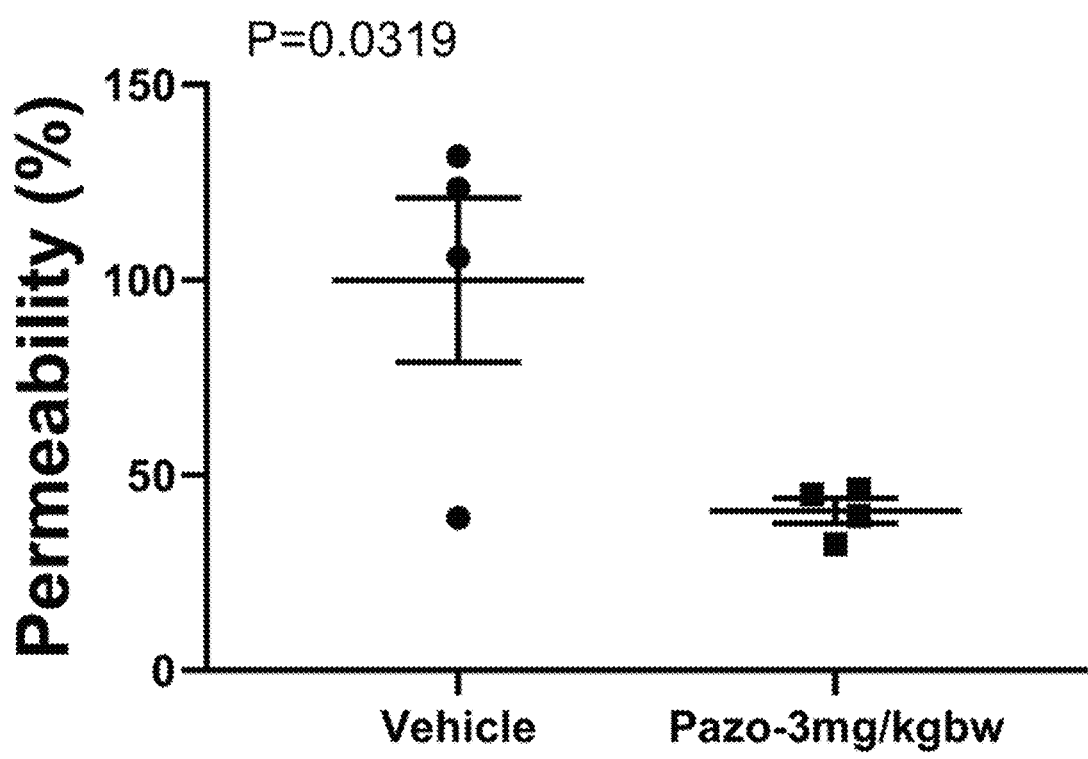
FIG. 3 shows pulmonary permeability in a mouse coronavirus induced acute lung injury model with one dose of a MAP3K2/MAP3K3 inhibitor given 24 hours after virus inoculation.

Conclusion:

As shown in FIG. 2, treatment with a pharmaceutical composition of pazopanib can significantly reduce pulmonary permeability in mouse coronavirus induced acute lung injury when 2 doses were given at 3 mg/kgbw.

Example 5: Efficacy Evaluation of One Dose of Pazopanib Composition Given 24 Hours After Virus Inoculation in Mouse Coronavirus Induced Lung Injury Model Purpose:

Evaluate the efficacy of pazopanib composition in coronavirus (Murine Hepatitis Virus Strain 1, MHV-1) induced mouse lung injury model.

Procedure:

a. Pazopanib Composition Preparation

1. Put 3.294 ml ddH2O in a small beaker with a small magnetic stir bar.
2. Weigh 1.663 g 2-Hydroxypropyl-beta-cyclodextrin (HP-b-CD).
3. Add HP-b-CD slowly into the water while stirring.
4. Keep stirring until HP-b-CD completely dissolved.
5. Transfer the HP-b-CD solution into a 15 ml tube.
6. Weigh 43 mg pazopanib hydrochloride and add it into HP-b-CD solution.
7. Vibrate the tube for 5 min followed by 30 min water bath sonication.
8. Then keep the tube in 50° C. for 30 min and pazopanib hydrochloride should be completely dissolved.

Vehicle Stock: 33.26% (332.6 mg/ml) HP-b-CD in ddH2O

Stock solution of pazopanib: 8.6 mg/ml in vehicle control

| | Vehicle Stock | Pazopanib stock |
|---|---|---|
| Vehicle control | 100 ul | 0 ul |
| 3 mg/kgbw | 93.03 ul | 6.97 ul |

* Each mouse is around 20 gbw and retro-orbital injection volume is 100 ul b. Animal Procedure A/J mice, 8-10 weeks old, were anaesthetized by Ketamine/Xylazine (100 mg/kg and 10 mg/kg) and were kept under anesthesia during the whole procedure using Ketamine/Xylazine. After being deeply anesthetized (assessed by applying a noxious stimulus, eg toe pinch, and observing no reflex response and no change in either the rate or character of respiration), mice received an intranasal inoculation of 6000 PFU MHV-1 in 20 μl Dulbecco's modified Eagle's medium. After the administration, the mice were monitored until their breathing gradually returned to normal. Then the mice were returned to the recovery cage on the heating pad and monitored for their anesthesia status. Twenty-four hours after the virus inoculation, vehicle control or 3 mg/kgbw pazopanib was delivered to mice via retro-orbital. Twenty-four hours after the drug administration, 100 μl of FITC-labeled albumin (10 mg/ml) was injected via the retro-orbital vein. Two hours after FITC-albumin injection, mice were euthanized and bronchoalveolar lavage (BAL) was collected via instilling 1 ml of PBS into the lungs, which was retrieved via a tracheal catheter. The green fluorescent of BAL was measured by the plate reader. BAL fluorescent intensities from pazopanib treated mice were normalized to the intensities from vehicle control-treated mice.

Conclusion:

As shown in FIG. 3, treatment with a pharmaceutical composition of pazopanib can significantly reduce pulmonary permeability in mouse coronavirus induced acute lung injury model when one dose (3 mg/kgbw) was given at 24 hr after virus inoculation.

Example 6: Efficacy Evaluation of One Dose of Pazopanib Composition Given 48 Hours after Virus Inoculation in Mouse Coronavirus Induced Lung Injury Model Purpose:

Evaluate the efficacy of pazopanib composition in coronavirus (Murine Hepatitis Virus Strain 1, MHV-1) induced mouse lung injury model.

Procedure:

a. Pazopanib Composition Preparation

1. Put 3.294 ml ddH2O in a small beaker with a small magnetic stir bar.
2. Weigh 1.663 g 2-Hydroxypropyl-beta-cyclodextrin (HP-b-CD).
3. Add HP-b-CD slowly into the water while stirring.
4. Keep stirring until HP-b-CD completely dissolved.
5. Transfer the HP-b-CD solution into a 15 ml tube.
6. Weigh 43 mg pazopanib hydrochloride and add it into HP-b-CD solution.
7. Vibrate the tube for 5 min followed by 30 min water bath sonication.
8. Then keep the tube in 50° C. for 30 min and pazopanib hydrochloride should be completely dissolved.

Vehicle Stock: 33.26% (332.6 mg/ml) HP-b-CD in ddH2O

Stock solution of pazopanib: 8.6 mg/ml in vehicle control

| | Vehicle Stock | Pazopanib stock |
|---|---|---|
| Vehicle control | 100 ul | 0 ul |
| 3 mg/kgbw | 93.03 ul | 6.97 ul |

* Each mouse is around 20 gbw and retro-orbital injection volume is 100 ul b. Animal Procedure A/J mice, 8-10 weeks old, were anaesthetized by Ketamine/Xylazine (100 mg/kg and 10 mg/kg) and were kept under anesthesia during the whole procedure using Ketamine/Xylazine. After being deeply anesthetized (assessed by applying a noxious stimulus, eg toe pinch, and observing no reflex response and no change in either the rate or character of respiration), mice received an intranasal inoculation of 6000 PFU MHV-1 in 20 µl Dulbecco's modified Eagle's medium. After the administration, the mice were monitored until their breathing gradually returned to normal. Then the mice were returned to the recovery cage on the heating pad and monitored for their anesthesia status. Forty-eight hours after the virus inoculation, vehicle control or 3 mg/kgbw pazopanib was delivered to mice via retro-orbital. Twenty-four hours after the drug administration, 100 µl of FITC-labeled albumin (10 mg/ml) was injected via the retro-orbital vein. Two hours after FITC-albumin injection, mice were euthanized and bronchoalveolar lavage (BAL) was collected via instilling 1 ml of PBS into the lungs, which was retrieved via a tracheal catheter. The green fluorescent of BAL was measured by the plate reader. BAL fluorescent intensities from pazopanib treated mice were normalized to the intensities from vehicle control-treated mice.

Figure 4:
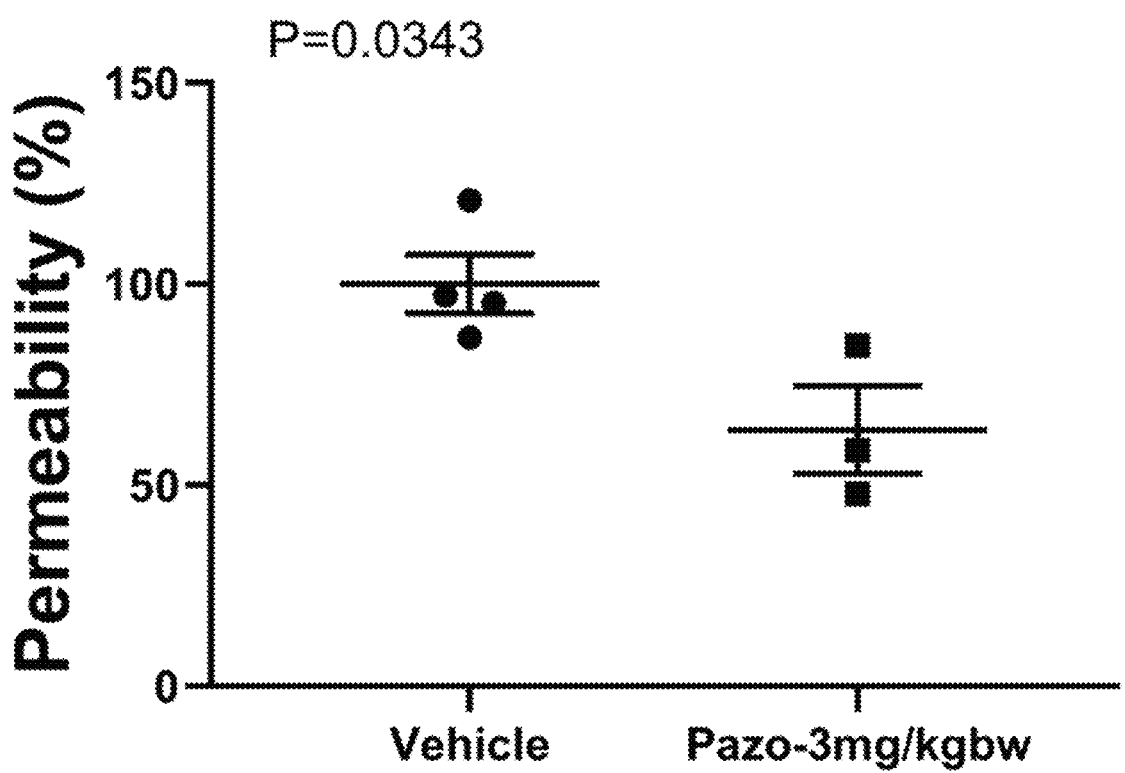
FIG. 4 shows pulmonary permeability in a mouse coronavirus induced acute lung injury model with one dose of a MAP3K2/MAP3K3 inhibitor given 48 hours after virus inoculation.

Conclusion:

As shown in FIG. 4, treatment with a pharmaceutical composition of pazopanib can significantly reduce pulmonary permeability in mouse coronavirus induced acute lung injury model when one dose (3 mg/kgbw) was given at 48 hr after virus inoculation.

Example 7: Efficacy Evaluation of One Dose of Pazopanib Composition Given 72 Hours after Virus Inoculation in Mouse Coronavirus Induced Lung Injury Model Purpose:

Evaluate the efficacy of pazopanib composition in coronavirus (Murine Hepatitis Virus Strain 1, MHV-1) induced mouse lung injury model.

Procedure:

a. Pazopanib Composition Preparation

1. Put 3.294 ml ddH2O in a small beaker with a small magnetic stir bar.
2. Weigh 1.663 g 2-Hydroxypropyl-beta-cyclodextrin (HP-b-CD).
3. Add HP-b-CD slowly into the water while stirring.
4. Keep stirring until HP-b-CD completely dissolved.
5. Transfer the HP-b-CD solution into a 15 ml tube.
6. Weigh 43 mg pazopanib hydrochloride and add it into HP-b-CD solution.
7. Vibrate the tube for 5 min followed by 30 min water bath sonication.
8. Then keep the tube in 50° C. for 30 min and pazopanib hydrochloride should be completely dissolved.

Vehicle Stock: 33.26% (332.6 mg/ml) HP-b-CD in ddH2O

Stock solution of pazopanib: 8.6 mg/ml in vehicle control

|  | Vehicle Stock | Pazopanib stock |
|---|---|---|
| Vehicle control | 100 ul | 0 ul |
| 3 mg/kgbw | 93.03 ul | 6.97 ul |

* Each mouse is around 20 gbw and retro-orbital injection volume is 100 ul b. Animal Procedure A/J mice, 8-10 weeks old, were anaesthetized by Ketamine/Xylazine (100 mg/kg and 10 mg/kg) and were kept under anesthesia during the whole procedure using Ketamine/Xylazine. After being deeply anesthetized (assessed by applying a noxious stimulus, eg toe pinch, and observing no reflex response and no change in either the rate or character of respiration), mice received an intranasal inoculation of 6000 PFU MHV-1 in 20 µl Dulbecco's modified Eagle's medium. After the administration, the mice were monitored until their breathing gradually returned to normal. Then the mice were returned to the recovery cage on the heating pad and monitored for their anesthesia status. Seventy-two hours after the virus inoculation, vehicle control or 3 mg/kgbw pazopanib was delivered to mice via retro-orbital. Twenty-four hours after the drug administration, 100 µl of FITC-labeled albumin (10 mg/ml) was injected via the retro-orbital vein. Two hours after FITC-albumin injection, mice were euthanized and bronchoalveolar lavage (BAL) was collected via instilling 1 ml of PBS into the lungs, which was retrieved via a tracheal catheter. The green fluorescent of BAL was measured by the plate reader. BAL fluorescent intensities from pazopanib treated mice were normalized to the intensities from vehicle control-treated mice.

Figure 5:
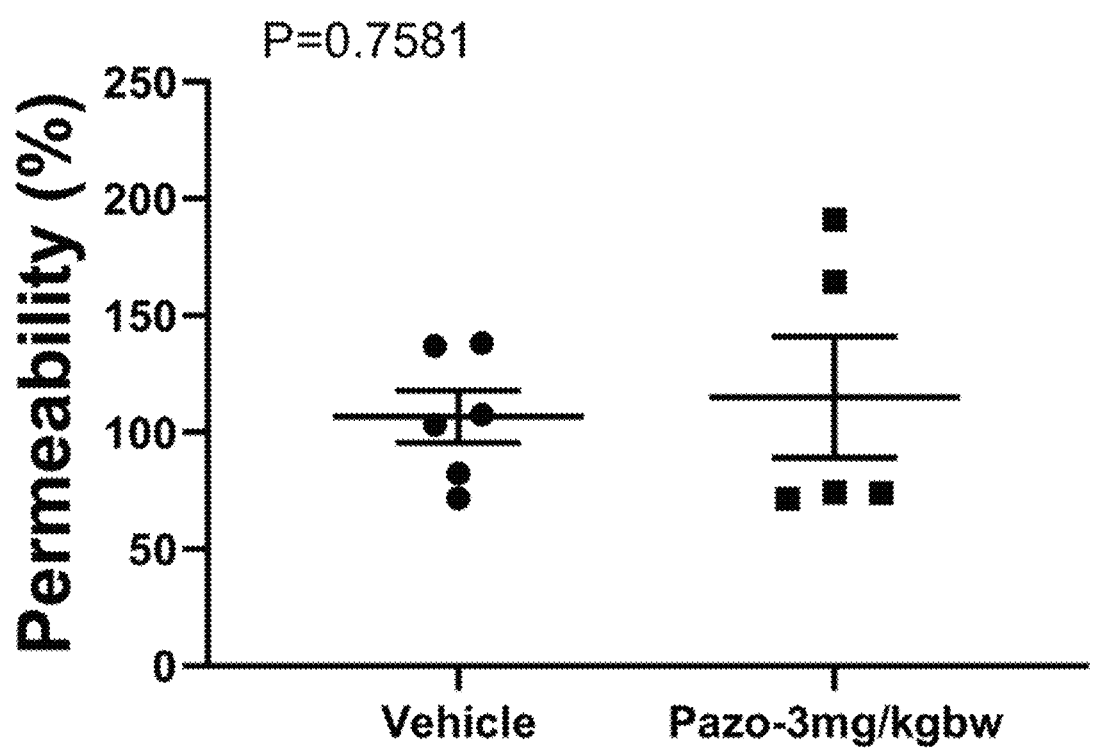
FIG. 5 shows pulmonary permeability in a mouse coronavirus induced acute lung injury model with one dose of a MAP3K2/MAP3K3 inhibitor given 72 hours after virus inoculation.

Conclusion:

As shown in FIG. 5, treatment with a pharmaceutical composition of pazopanib has a negligible effect on pulmonary permeability in mouse coronavirus induced acute lung injury model when one dose (3 mg/kgbw) was given at 72 hr after virus inoculation.

Example 8: Efficacy Evaluation of Pazopanib Composition in Body Weight Loss and Survival Probability of Mouse Coronavirus Induced Lung Injury Model Purpose:

Evaluate the efficacy of pazopanib composition in coronavirus (Murine Hepatitis Virus Strain 1, MHV-1) induced mouse lung injury model.

Procedure:

a. Pazopanib Composition Preparation

1. Put 3.294 ml ddH2O in a small beaker with a small magnetic stir bar.
2. Weigh 1.663 g 2-Hydroxypropyl-beta-cyclodextrin (HP-b-CD).
3. Add HP-b-CD slowly into the water while stirring.
4. Keep stirring until HP-b-CD completely dissolved.
5. Transfer the HP-b-CD solution into a 15 ml tube.
6. Weigh 43 mg pazopanib hydrochloride and add it into HP-b-CD solution.
7. Vibrate the tube for 5 min followed by 30 min water bath sonication.
8. Then keep the tube in 50° C. for 30 min and pazopanib hydrochloride should be completely dissolved.

Vehicle Stock: 33.26% (332.6 mg/ml) HP-b-CD in ddH2O

Stock solution of pazopanib: 8.6 mg/ml in vehicle control

|  | Vehicle Stock | Pazopanib stock |
| --- | --- | --- |
| Vehicle control | 100 ul | 0 ul |
| 3 mg/kgbw | 93.03 ul | 6.97 ul |

* Each mouse is around 20 gbw and retro-orbital injection volume is 100 ul b. Animal Procedure A/J mice, 8-10 weeks old, were anaesthetized by Ketamine/Xylazine (100 mg/kg and 10 mg/kg) and were kept under anesthesia during the whole procedure using Ketamine/Xylazine. After being deeply anesthetized (assessed by applying a noxious stimulus, eg toe pinch, and observing no reflex response and no change in either the rate or character of respiration), mice received an intranasal inoculation of 6000 PFU MHV-1 in 20 µl Dulbecco's modified Eagle's medium. After the administration, the mice were monitored until their breathing gradually returned to normal. Then the mice were returned to the recovery cage on the heating pad and monitored for their anesthesia status. Vehicle control or 3 mg/kgbw pazopanib was delivered to mice via retro-orbital once daily since 24 hr after the virus inoculation. The last dose was given on 120 hr after the virus inoculation. The mice were monitored twice daily. Survival and body weight were recorded.

Figure 6:
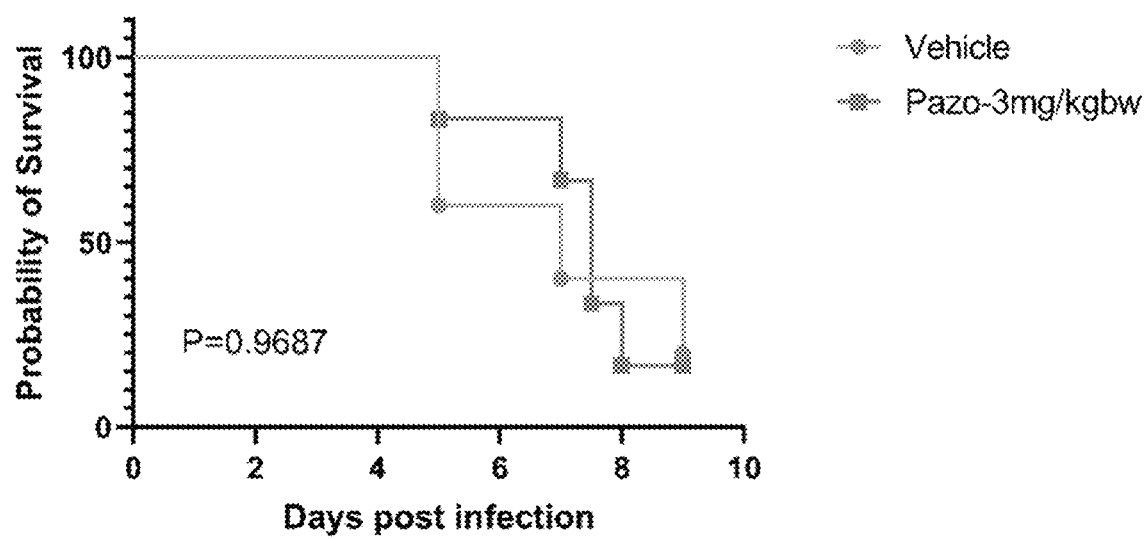
FIG. 6 shows probability of survival in a mouse coronavirus induced acute lung injury model with daily doses of a MAP3K2/MAP3K3 inhibitor.
Figure 7:
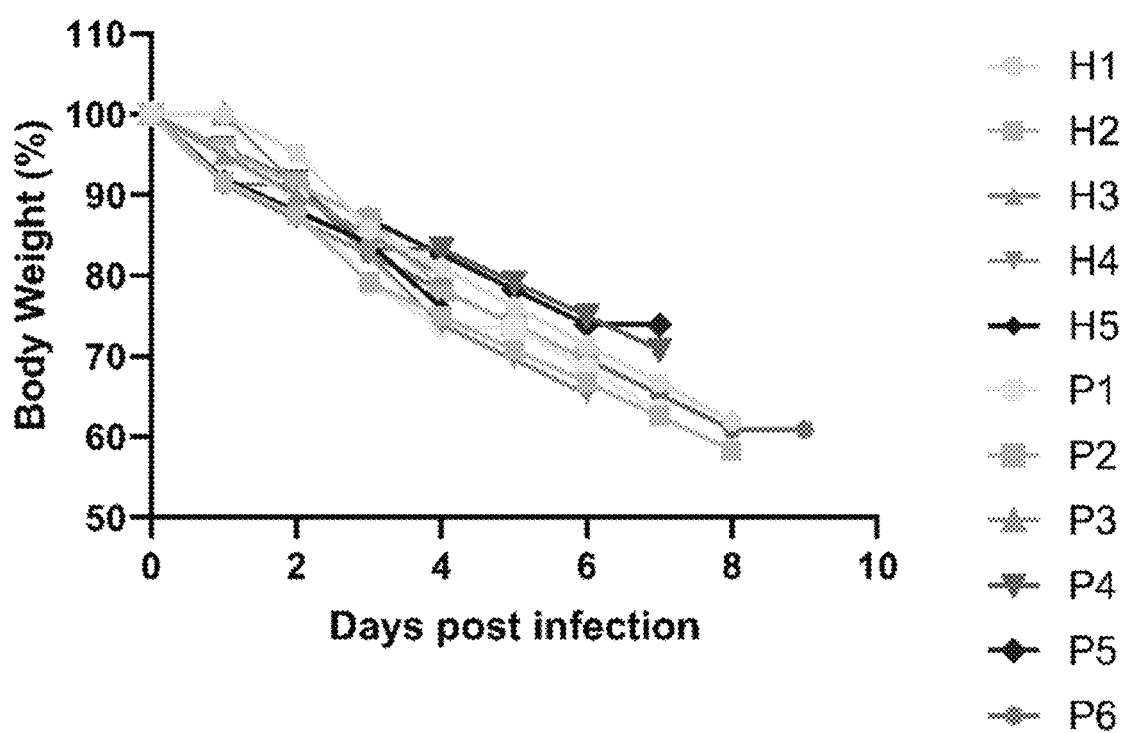
FIG. 7 shows body weight loss in a mouse coronavirus induced acute lung injury model with daily doses of a MAP3K2/MAP3K3 inhibitor.

Conclusion:

As shown in FIGS. 6 and 7, treatment with a pharmaceutical composition of pazopanib does not affect survival rate or body weight loss in mouse coronavirus induced acute lung injury model when one dose was given daily for 5 days since 24 hr after virus inoculation. These results are not contrary to or unsupportive of the results in Examples 3-6 that sufficiently early intervention with a pazopanib composition reduces viral-induced lung injury as quantified by pulmonary permeability.

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and compositions of the present invention, where the term comprises is used with respect to the recited steps of the methods or components of the compositions, it is also contemplated that the methods and compositions consist essentially of, or consist of, the recited steps or components. Furthermore, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as being composed of the components prior to mixing, because upon mixing certain components can further react or be transformed into additional materials.

All percentages and ratios used herein, unless otherwise indicated, are by weight. It is recognized the mass of an object is often referred to as its weight in everyday usage and for most common scientific purposes, but that mass technically refers to the amount of matter of an object, whereas weight refers to the force experienced by an object due to gravity. Also, in common usage the "weight" (mass) of an object is what one determines when one "weighs" (masses) an object on a scale or balance.

What is claimed is:

1. A method for treating, preventing, or reducing the severity of a lung injury associated with a coronavirus infection comprising administering to a human subject in need thereof a therapeutically effective amount of pazopanib, or a pharmaceutically acceptable salt or solvate thereof.

2. The method of claim 1 wherein the coronavirus infection is caused by the Severe Acute Respiratory Syndrome Corona Virus 2 (SARS-CoV-2).

3. The method of claim 1 wherein the pharmaceutically acceptable salt is selected from a salt of a mineral acid selected from the group consisting of hydrochloride, hydrobromide, hydroiodide, hydrogen sulfate, or a salt selected from mesylate, esylate, besylate, tosylate, and combinations thereof.

4. The method of claim 3 wherein the pharmaceutically acceptable salt is the hydrochloride salt.

5. The method of claim 1 wherein the pazopanib, or a pharmaceutically acceptable salt or solvate thereof is administered using an administration route selected from the group consisting of oral, intra venous, parenteral, nasal, inhalation, intratracheal, intrapulmonary, and intrabronchial.

6. The method of claim 5 wherein the administration is selected from the group consisting of oral, parenteral, nasal, inhalation, intratracheal, intrapulmonary, and intrabronchial, and the administration is performed using a spray device or nebulizer.

7. The method of claim 1 wherein the lung injury is lung fibrosis.

8. The method of claim 1 wherein the lung injury is selected from the group consisting of acute lung injury (ALI) and acute respiratory distress syndrome (ARDS).

9. The method of claim 1 wherein the lung injury involves pulmonary edema, and wherein the pulmonary edema is reduced after treatment.

10. The method of claim 1 wherein the patient experiences one or more improvements of condition after treatment selected from the group consisting of: reduced time on ventilator, improved blood oxygen levels, an increase in rheumatoid factor (RF) production from neutrophils, an increase in reactive oxygen species (ROS), reduced recovery time, reduced pulmonary permeability, improved pulmonary barrier function, increased pulmonary barrier cell survival.

11. The method of claim 1 wherein the pazopanib, or a pharmaceutically acceptable salt or solvate thereof is administered from the group consisting of about four times per day, about three times per day, about two times per day, about one time per day, about one time every other day, about two times per week, and about one time per week.

12. The method of claim 11 wherein the pazopanib, or a pharmaceutically acceptable salt or solvate thereof is administered for a period selected from the group consisting of about 1 day to about 30 days, about 1 day to about 1 month, about 1 day to about 14 days, about 1 day to about 10 days, about 1 day to about 1 week, about 1 day to about 5 days, about 1 day to about 3 days, and until the infection is treated.

13. The method of claim 12 wherein at least one of the following pharmacokinetic parameters achieved in the patient is selected from the group consisting of an AUC of about 1,037 mcg*h/mL or a Cmax of about 58.1 mcg/mL (equivalent to about 132 μM).

14. The method of claim 1 wherein the pazopanib, or a pharmaceutically acceptable salt or solvate thereof is administered at about 100 mg, or about 200 mg, or about 300 mg, or about 400 mg, or about 500 mg or about 600 mg, or about 700 mg, or about 800 mg per unit dosage.

15. The method of claim 1 wherein the pazopanib, or a pharmaceutically acceptable salt or solvate thereof is administered at about 100 mg, or about 150 mg, or about 200 mg, or about 250 mg, or about 300 mg per unit dosage.

16. The method of claim 15 wherein the pazopanib, or a pharmaceutically acceptable salt or solvate thereof is administered at about 150 mg per unit dosage.

17. The method of claim 1 wherein the pazopanib, or a pharmaceutically acceptable salt or solvate thereof is administered about two times per day.

18. The method of claim 15 wherein the pazopanib, or a pharmaceutically acceptable salt or solvate thereof is administered about two times per day.

19. A method for treating or reducing the severity of a lung injury associated with a coronavirus infection comprising administering to a human subject in need thereof a therapeutically effective amount of a pharmaceutical composition comprising:
pazopanib or a pharmaceutically acceptable salt or solvate thereof.

20. The method of claim 19 wherein the coronavirus infection is caused by the Severe Acute Respiratory Syndrome Corona Virus 2 (SARS-CoV-2).

21. The method of claim 19 wherein the pharmaceutical composition further comprises an anti-viral agent.

22. The method of claim 19 wherein the lung injury is selected from the group consisting of acute lung injury (ALI), lung fibrosis, and acute respiratory distress syndrome (ARDS).

23. The method of claim 19 wherein the pharmaceutical composition comprises from about 1 to about 1000 mg per unit dosage of pazopanib, or a pharmaceutically acceptable salt or solvate thereof.

24. The method of claim 19 wherein the pharmaceutical composition comprises about 100 mg, or about 200 mg, or about 300 mg, or about 400 mg, or about 500 mg or about 600 mg, or about 700 mg, or about 800 mg per unit dosage of pazopanib, or a pharmaceutically acceptable salt or solvate thereof.

25. The method of claim 19 wherein the pharmaceutical composition comprises about 100 mg, or about 150 mg, or about 200 mg, or about 250 mg, or about 300 mg of nintedanib, or a pharmaceutically acceptable salt or solvate thereof.

26. The method of claim 19 wherein the pharmaceutical composition comprises about 150 mg of pazopanib, or a pharmaceutically acceptable salt or solvate thereof.

27. The method of claim 19 wherein the pharmaceutical composition is administered according to a regimen selected from the group consisting of about four times per day, about three times per day, about two times per day, about one time per day, about one time every other day, about two times per week, and about one time per week.

28. The method of claim 19 wherein the pharmaceutical composition is administered about two times per day.

29. The method of claim 19 wherein the pharmaceutical composition is administered about two times per day.

30. The method of claim 19 wherein the pharmaceutical composition is administered for a period selected from the group consisting of about 1 day to about 30 days, about 1 day to about one month, about 1 day to about 14 days, about 1 day to about 10 days, about 1 day to about 1 week, about 1 day to about 5 days, about 1 day to about 3 days, and until the infection is treated.

31. The method of claim 21, wherein the anti-viral agent is remdesivir, or a pharmaceutically acceptable salt, ester, or solvate thereof.

* * * * *